US012433820B2

(12) United States Patent
Liu

(10) Patent No.: US 12,433,820 B2
(45) Date of Patent: Oct. 7, 2025

(54) SYSTEMS AND METHODS FOR CONTROLLING VIBROTACTILE OUTPUT OF ADULT TOYS

(71) Applicant: HYTTO PTE. LTD., Singapore (SG)

(72) Inventor: Dan Liu, Guangzhou (CN)

(73) Assignee: HYTTO PTE. LTD., Singapore (SG)

( * ) Notice: Subject to any disclaimer, the term of this patent is extended or adjusted under 35 U.S.C. 154(b) by 1123 days.

(21) Appl. No.: 17/221,823

(22) Filed: Apr. 4, 2021

(65) Prior Publication Data

US 2024/0091097 A1 Mar. 21, 2024

Related U.S. Application Data

(63) Continuation-in-part of application No. 16/369,143, filed on Mar. 29, 2019, now Pat. No. 10,999,608.

(51) Int. Cl.
*A61H 19/00* (2006.01)
*A61H 23/00* (2006.01)
*G16H 20/30* (2018.01)

(52) U.S. Cl.
CPC ............ *A61H 23/00* (2013.01); *A61H 19/00* (2013.01); *G16H 20/30* (2018.01); *A61H 2201/5012* (2013.01); *A61H 2201/5015* (2013.01); *A61H 2201/5023* (2013.01); *A61H 2201/5097* (2013.01)

(58) Field of Classification Search
None
See application file for complete search history.

(56) References Cited

U.S. PATENT DOCUMENTS 6,368,268 B1 * 4/2002 Sandvick ............... A61H 19/32 600/38
7,446,752 B2 11/2008 Goldenberg et al.
8,089,458 B2 1/2012 Barney et al.
8,608,644 B1 * 12/2013 Davig ....................... A61F 5/00 600/38
8,814,688 B2 8/2014 Barney et al.
9,132,058 B2 * 9/2015 Imboden ................ A61H 19/00
9,492,847 B2 11/2016 Goldenberg et al.
9,993,724 B2 6/2018 Barney et al.
10,583,357 B2 3/2020 Barney et al.
(Continued)

*Primary Examiner* — LaToya M Louis
(74) *Attorney, Agent, or Firm* — Holtz, Holtz & Volek PC

(57) ABSTRACT

Systems and methods for controlling vibrotactile output of adult toys. The method performed by the server system includes receiving a user input from a user device associated with a first user of a plurality of users. The user input includes an interaction information for controlling the vibrotactile output of a second adult toy associated with a second user of the plurality of users. The method includes generating a control pattern in response to the interaction information. The control pattern includes parameters related to timing and intensity of the vibrotactile output corresponding to the interaction information. Further the method includes transmitting the control pattern to a user device associated with the second user for operating the second adult toy to provide the vibrotactile output to the second user. The vibrotactile output of the control pattern proportionally reproduces the interaction information provided by the first user.

16 Claims, 17 Drawing Sheets

(56) References Cited

U.S. PATENT DOCUMENTS

| | | | | |
|---|---|---|---|---|
| 2004/0082831 | A1 * | 4/2004 | Kobashikawa ........ | A61H 19/32 600/38 |
| 2013/0116502 | A1 * | 5/2013 | Cambridge ........ | G06Q 30/0601 600/38 |
| 2013/0215116 | A1 * | 8/2013 | Siddique ................ | G06Q 20/40 705/26.7 |
| 2015/0328082 | A1 * | 11/2015 | Jiang ...................... | A61H 23/02 600/38 |

* cited by examiner

SYSTEMS AND METHODS FOR CONTROLLING VIBROTACTILE OUTPUT OF ADULT TOYS

TECHNICAL FIELD

The present disclosure relates to systems and methods for controlling vibrotactile output of adult toys and, more particularly relates, to the systems and methods for controlling the vibrotactile output of the adult toys for providing physical pleasure or sexual stimulation for users in remote locations.

BACKGROUND

Sexual stimulation can be achieved by an individual or a group of individuals (irrespective of gender) by using adult toys. The adult toys are generally simple and can have a vibration feature for providing sexual stimulation. In conventional adult toys, a degree of sexual stimulation may be manually controlled, for example, the adult toys may be configured with an on/off switch. However, as these conventional adult toys are self-operated by the individual for experiencing sexual stimulation by using a single setting in the adult toy, the individual may not always feel the same level of stimulation at every instance using the adult toy. Additionally, the arousals of the individual may change periodically based on mood and environment, thus the stimulation produced by the adult toy using the single vibration setting may not satisfy the individual.

Currently, the social media and ability to extend wireless interfaces, local and wide area networking etc., have contributed to configurability of the adult toys. These technologies provide a level of customization to the needs of the individual or the group of individuals to experience sexual stimulation without direct physical contact. However, these technologies require built-in sensors in the adult toys for collecting behavioral characteristics of the individual in order to operate the adult toy for providing sexual stimulation. In some cases, the sensors may not appropriately determine the behavioral characteristics of the individual. This leads to a poor understanding of the behavioral and/or psychological characteristics of the two individuals located remotely. Hence, the adult toys may not be operated according to the behavioral characteristics of the individuals.

Therefore, there is a need for techniques to overcome one or more limitations stated above in addition to providing other technical advantages.

SUMMARY

Various embodiments of the present disclosure provide systems and methods for controlling vibrotactile output of adult toys.

In an embodiment, a method for controlling a vibrotactile output of an adult toy is disclosed. The method performed by a server system includes receiving a user input from a user device associated with a first user of a plurality of users. The user input includes an interaction information for controlling the vibrotactile output of a second adult toy associated with a second user of the plurality of users. The method includes generating a control pattern in response to the interaction information from the first user. The control pattern includes parameters related to timing and intensity of the vibrotactile output corresponding to the interaction information. Further, the method includes transmitting the control pattern to a user device associated with the second user for operating the second adult toy to provide the vibrotactile output to the second user. The vibrotactile output of the control pattern proportionally reproduces the interaction information provided by the first user.

In another embodiment, a server system for controlling a vibrotactile output of an adult toy is disclosed. The server system includes a communication interface, memory storing executable instructions and a processor operatively coupled with the communication interface and the memory. The processor is configured to execute the executable instructions to cause the system to at least receive a user input from a user device associated with a first user of a plurality of users. The user input includes an interaction information for controlling the vibrotactile output of a second adult toy associated with a second user of the plurality of users. The server system is further caused to generate a control pattern in response to the interaction information from the first user. The control pattern includes parameters related to timing and intensity of the vibrotactile output corresponding to the interaction information. The server system is caused to transmit the control pattern to a user device associated with the second user for operating the second adult toy to provide the vibrotactile output to the second user. The vibrotactile output of the control pattern proportionally reproduces the interaction information provided by the first user.

BRIEF DESCRIPTION OF THE FIGURES

The following detailed description of illustrative embodiments is better understood when read in conjunction with the appended drawings. For the purpose of illustrating the present disclosure, exemplary constructions of the disclosure are shown in the drawings. However, the present disclosure is not limited to a specific device or a tool and instrumentalities disclosed herein. Moreover, those in the art will understand that the drawings are not to scale. Wherever possible, like elements have been indicated by identical numbers.

Figure 1:
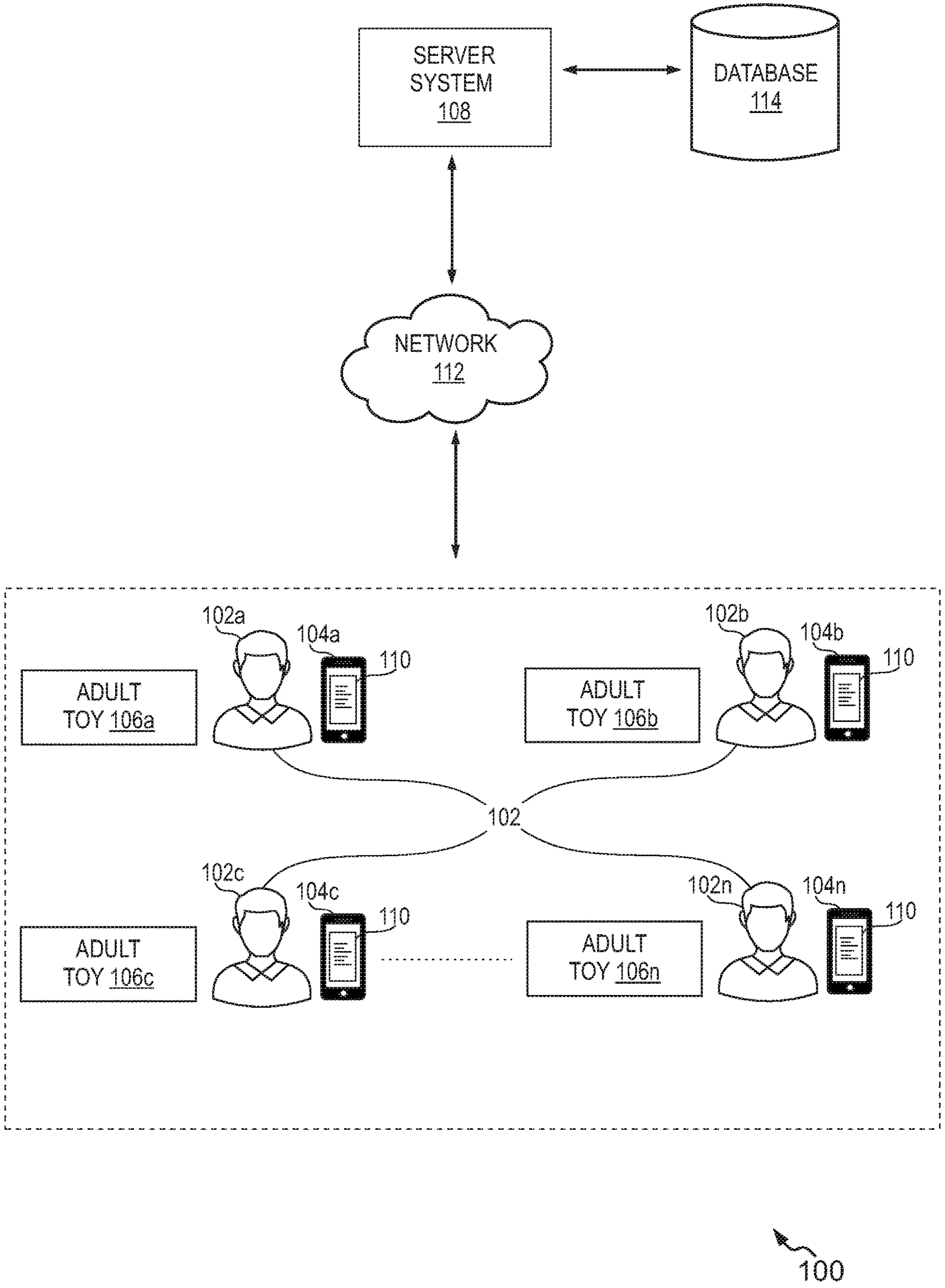
FIG. 1 illustrates an example representation of an environment, in which at least some embodiments of the present disclosure can be implemented.

The drawings referred to in this description are not to be understood as being drawn to scale except if specifically noted, and such drawings are only exemplary in nature.

DETAILED DESCRIPTION

In the following description, for purposes of explanation, numerous specific details are set forth in order to provide a thorough understanding of the present disclosure. It will be apparent, however, to one skilled in the art that the present disclosure can be practiced without these specific details. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

Reference in this specification to "one embodiment" or "an embodiment" means that a particular feature, structure, or characteristic described in connection with the embodiment is included in at least one embodiment of the present disclosure. The appearances of the phrase "in an embodiment" in various places in the specification are not necessarily all referring to the same embodiment, nor are separate or alternative embodiments mutually exclusive of other embodiments. Moreover, various features are described which may be exhibited by some embodiments and not by others. Similarly, various requirements are described which may be requirements for some embodiments but not for other embodiments.

Moreover, although the following description contains many specifics for the purposes of illustration, anyone skilled in the art will appreciate that many variations and/or alterations to said details are within the scope of the present disclosure. Similarly, although many of the features of the present disclosure are described in terms of each other, or in conjunction with each other, one skilled in the art will appreciate that many of these features can be provided independently of other features. Accordingly, this description of the present disclosure is set forth without any loss of generality to, and without imposing limitations upon, the present disclosure.

The terms "wiping" or "cleaning" refers to any shearing action that a cleaning pad or a substrate undergoes while in contact with a target surface. This includes hand or body motion, substrate-implement motion over a surface.

Overview

Various embodiments of the present disclosure provide systems and methods for controlling vibrotactile output of adult toys.

The present disclosure describes a server system that is configured to control the vibrotactile output of the adult toy through an interactive application installed in a user device. In an embodiment, the server system is configured to receive a user input from a user device associated with a first user of a plurality of users. The user input may be provided in form of a text input, a gesture input or an audio input by the users in the application. The user input includes an interaction information that is used for controlling the vibrotactile output of a second adult toy associated with a second user of the plurality of users. Then, the server system generates a control pattern in response to the interaction information from the first user. In one scenario, if the user input is received in form of the text input, the server system may convert the text format by using a code table for creating the control pattern. In another scenario, the server system is configured to create the control pattern from the audio input either by analyzing the volume associated with the audio input, or converting the audio input to a text format for creating the control pattern. In yet another scenario, the server system is configured to create the control pattern by using the gesture input from the first user. Further, the server system is configured to adjust parameters related to the timing and intensity of the vibrotactile output corresponding to the interaction information, thus enabling the control pattern to vibrate as per the adjusted timing and intensity. Thereafter, the server system is configured to transmit the control pattern to a user device associated with the second user for operating the second adult toy to provide the vibrotactile output to the second user. The vibrotactile output of the control pattern proportionally reproduces the interaction information provided by the first user, thus enabling the second user to understand the text input, gesture input, or the audio input by feeling the vibration produced by the adult toy of the second user.

Additionally, the server system may automatically connect two users in the interactive application as friends based on recognizing a user input of the control pattern of one user by another user of the application. More specifically, the server system is configured to receive a decrypted information from the first user in response to sensing the vibrotactile output associated with a control pattern of the second user by using a first adult toy of the first user. Further, the server system validates the decrypted information with a user input of the second user provided in the interactive application while creating the control pattern. Thereafter, the server system is configured to facilitate a connection between the first user and the second user of the plurality of users as friends in the interactive application, if the decrypted information received from the first user matches with the user input provided by the second user.

Further, the server system combines one or more control patterns from the first user based at least on the sequence and playback speed associated with each control pattern of the one or more control patterns. Furthermore, the server system is configured to transmit a broadcast code received from a broadcast host of the interactive application to the plurality of users. The server system transmits a confirmation message indicative of approval for the broadcasting show from at least one user of the plurality of users who entered the broadcast code in the application. Thereafter, the server system broadcasts a control pattern received from the host to at least one user for enabling the adult toy of at least one user to vibrate along with the adult toy of the host during the broadcasting show.

Various embodiments of the present invention are described hereinafter with reference to FIG. 1 to FIG. 10.

FIG. 1 illustrates an example representation of an environment 100, in which at least some example embodiments of the present disclosure can be implemented. The environment 100 is depicted to include a plurality of users 102 (collectively referred for a first user 102*a*, a second user 102*b*, a third user 102*c* . . . user 102*n*). Each user of the plurality of users 102 is associated with an electronic device, such as a user device 104*a*, a user device 104*b*, a user device 104*c* . . . a user device 104*n*. Some examples of the user device 104*a*-104*n* may include, but are not limited to, laptops, smartphones, desktops, tablets, wearable devices, workstation terminals, and the like. The user devices 104*a*-104*n* may be equipped with an instance of an application, such as an application 110 installed therein. The environment 100 includes a first adult toy 106*a*, a second adult toy 106*b*, a third adult toy 106*c* . . . adult toy 106*n* associated with the corresponding users 102*a*-102*n*. Examples of adult toys may include, but are not limited to, a dildo, a vibrator and the like. The adult toys 106*a*-106*n* may be connected wirelessly with the user devices 104*a*-104*n*. Some examples of the wireless connectivity for enabling connection between the adult toys and the user devices may be, but are not limited to, near field communication (NFC), wireless fidelity (Wi-Fi), Bluetooth and the like.

The application 110 is an interactive application that provides a virtual platform for providing sexual stimulation to the users (e.g., the users 102*a* and 102*b*) by using their corresponding adult toys (e.g., the adult toys 106*a* and 106*b*). It should be noted that the user 102*a* may interact with other users, such as the users 102*b*-102*n* located either in remote locations and/or present physically through the interactive application 110. Further, one or more components associated with the interactive application 110 may rest in a server system 108 and the user devices 104*a*-104*n*.

The user device (e.g., the user device 104*a*) can communicate with the server system 108 through the application 110 via a network 112. The network 112 may include, without limitation, a local area network (LAN), a wide area network (WAN) (e.g., the Internet, etc.), a mobile network, a virtual network, and/or another suitable public and/or private network capable of supporting communication among two or more of the components or the users illustrated in FIG. 1, or any combination thereof. Various entities in the environment 100 may connect to the network 112 in accordance with various wired and wireless communication protocols, such as Transmission Control Protocol and Internet Protocol (TCP/IP), User Datagram Protocol (UDP), 2nd Generation (2G), 3rd Generation (3G), 4th Generation (4G), 5th Generation (5G) communication protocols, Long Term Evolution (LTE) communication protocols, or any combination thereof.

The user (e.g., the user 102*a*) may provide a user input including an interactive information through the application 110 to the server system 108 via the network 112. The user input including the interaction information is used for controlling a vibrotactile output of the adult toy 106*b* of the user 102*b*. The user input may be a text input, a voice and/or audio input, and a gesture input. Upon receiving the user input, the server system 108 may be configured to create a control pattern based on the user input. Further, the control pattern created by the server system 108 may be transmitted to at least the user device 104*a* (or creator of the pattern, such as user 102*a*) and a database 114 communicably coupled to the server system 108 for storage.

Thereafter, the control pattern may be transmitted by the server system 108 to the user device 104*b* of the user 102*b*. The user 102*b* may operate the adult toy 106*b* by using the user device 104*b* by using the control pattern received from the user 102*a*. The adult toy 106*b* produces the vibrotactile output to the user 102*b* based on the control pattern so as to proportionally reproduce the interaction information provided by the first user. This enables the user 102*b* to sense and/or understand the interactive information provided by the user 102*a* by experiencing the sexual stimulation caused by the vibrotactile output of the adult toy 106*b*. In other words, the user device 104*b* can control the adult toy 106*b* to vibrate according to the control pattern of the user 102*a*, thus enabling user 102*b* at the remote location to understand the interactive information provided by the user 102*a* by using the adult toy 106*b*.

Figure 2:
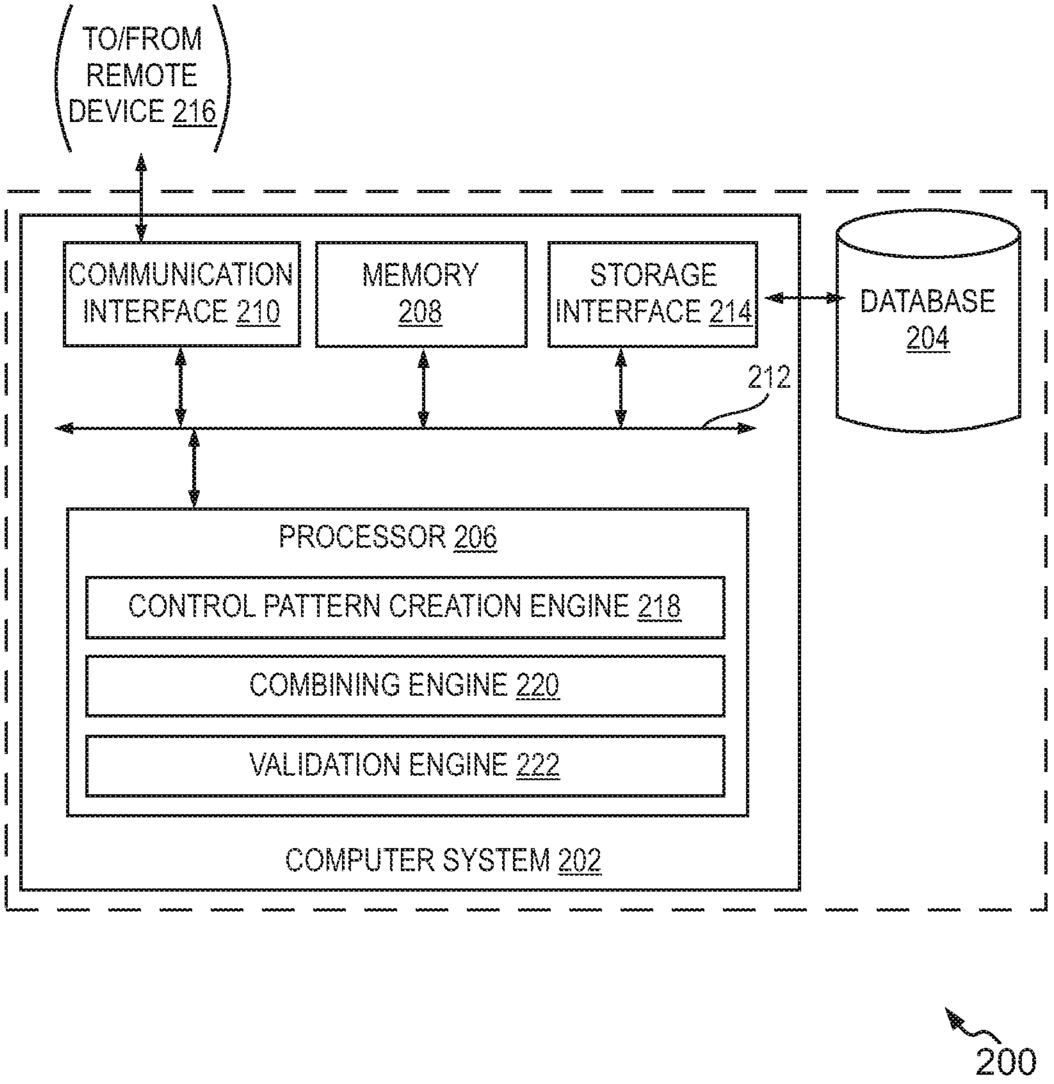
FIG. 2 illustrates a simplified block diagram of a server system used for controlling vibrotactile output of adult toys associated with users located in remote locations, in accordance with one embodiment of the present disclosure.

FIG. 2 illustrates a simplified block diagram of a server system 200 used for controlling the vibrotactile output of the adult toys associated with the users located in remote locations via the application 110, in accordance with one embodiment of the present disclosure. The server system 200 is an example of the server system 108 as shown and described with reference to FIG. 1. The server system 200 includes a computer system 202 and a database 204. The computer system 202 includes at least one processor 206 for executing instructions, a memory 208, a communication interface 210, and a storage interface 214. The one or more components of the computer system 202 communicate with each other via a bus 212.

In one embodiment, the database 204 is integrated within the computer system 202 and configured to store an instance of the interactive application 110 and one or more components of the interactive application 110. The one or more components of the application 110 may be, but not limited to, information related to user inputs, parameters associated with the conversion of user inputs to the control pattern, the control pattern of the users 102, user profiles associated with the users 102 and the like. The computer system 202 may include one or more hard disk drives as the database 204. The storage interface 214 is any component capable of providing the processor 206 an access to the database 204. The storage interface 214 may include, for example, an Advanced Technology Attachment (ATA) adapter, a Serial ATA (SATA) adapter, a Small Computer System Interface (SCSI) adapter, a RAID controller, a SAN adapter, a network adapter, and/or any component providing the processor 206 with access to the database 204.

The processor 206 includes a suitable logic, circuitry, and/or interfaces to execute computer-readable instructions for performing one or more operations to provide the virtual platform for the users 102 through the application 110 for experiencing the sexual stimulation between the users 102 located in remote locations. Examples of the processor 206 include, but are not limited to, an application-specific integrated circuit (ASIC) processor, a reduced instruction set computing (RISC) processor, a complex instruction set computing (CISC) processor, a field-programmable gate array (FPGA), and the like. The memory 208 includes a suitable logic, circuitry, and/or interfaces to store a set of computer-readable instructions for performing the operations. Examples of the memory 208 include a random-access memory (RAM), a read-only memory (ROM), a removable storage drive, a hard disk drive (HDD), and the like. In some embodiments, the memory 208 may be realized in the form of a database server or a cloud storage working in conjunction with the server system 200, without deviating from the scope of the present disclosure.

The processor 206 is operatively coupled to the communication interface 210 such that the processor 206 is capable of communicating with a remote device 216 such as, the user devices 104*a*-104*n*, the database 114, or with any entity connected to the network 112 as shown in FIG. 1.

It is noted that the server system 200 as illustrated and hereinafter described is merely illustrative of an apparatus that could benefit from embodiments of the present disclosure and, therefore, should not be taken to limit the scope of the present disclosure. It is noted that the server system 200 may include fewer or more components than those depicted in FIG. 2.

In one embodiment, the processor 206 includes a control pattern creation engine 218, a combining engine 220, and a validation engine 222. As such, the one or more components of the processor 206 as described above are communicably coupled with the application 110 and configured to manage the vibrotactile output of the adult toys 106*a*-106*n* associated with the users 102*a*-102*n*.

The control pattern creation engine 218 includes a suitable logic and/or interfaces for creating the control pattern based on receipt of the user inputs (either, the text input, the audio and/or voice input, and the gesture input) through the application 110. In one scenario, the server system 200 may receive the text input through the application 110 on the user device 104*a* of the user 102*a*. The control pattern creation engine 218 of the server system 200 may be configured to analyze the text input and create the control pattern by converting the text input into a pattern (such as, the control pattern). More specifically, the control pattern creation engine 218 may be configured to create the control pattern by encrypting the interactive information and/or the user inputs in form of a code (e.g., Morse code). Additionally, or alternatively, the control pattern creation engine 218 may use any other coding techniques as per feasibility and requirement for creating the control pattern. Further, the control pattern creation engine 218 may be configured to decide the vibrotactile output for the control pattern in order to control the adult toy (e.g., the adult toy 106*b*) of the user, such as the user 102*b*. Particularly, the control pattern creation engine 218 may adjust parameters related to timing and intensity of the vibrotactile output corresponding to the interaction information. Thereafter, the control pattern is transmitted by the server system 200 to the user device 104*b* of the user 102*b*. The user 102*b* operates the adult toy 106*b* in the control pattern's way created by the user 102*a*. To that effect, the user 102*b* at the remote location can understand the text input provided by the user 102*a* by sensing the vibrotactile output provided by the adult toy 106*b*.

In another scenario, the server system 200 may receive the audio input through the application 110 on the user device 104*a* of the user 102*a*. In one example scenario, the user 102*a* may send a pre-stored and/or default audio track provided by the application 110 to the server system 200. In another example scenario, the user 102*a* may send an audio file stored in a local repository of the user device 104*b* to the server system 200. In another scenario, the user 102*a* may use an option provided by the application 110 for recording the audio of the user 102*a*. The recorded audio is transmitted as the audio input to the server system 200 by the user 102*a*. In one case, the control pattern creation engine 218 of the server system 200 may be configured to analyze a volume (or amplitude of sound wave) associated with the audio input. Thereafter, the control pattern creation engine 218 may be configured to create the control pattern based on the volume of the audio input. More specifically, the control pattern creation engine 218 may be configured to create the control pattern by encrypting the audio input (i.e. interactive information). In another case, the control pattern creation engine 218 of the server system 200 may be configured to convert the audio input into a text format by using a speech-to-text conversion technique. The control pattern creation engine 218 may be configured to create the control pattern based on the text format of the audio input. More specifically, the control pattern creation engine 218 may be configured to create the control pattern by encrypting the text format of the audio input (i.e. interactive information) as explained above. Similarly, the control pattern creation engine 218 may be configured to decide the vibrotactile output for the control pattern created by the audio input by adjusting the parameters such as, the timing and the intensity as explained above.

Thereafter, the control pattern created by the server system 200 as explained in both the cases is transmitted to the user device 104*b* of the user 102*b*. The user 102*b* can operate the adult toy 106*b* in the control pattern's way created by the user 102*a*. To that effect, the user 102*b* at the remote location can understand the audio input (or a music without hearing the sound) provided by the user 102*a* by the sexual stimulation caused by the vibrotactile output of the adult toy 106*b*.

In yet another scenario, the server system 200 may receive the gesture input through the application 110 on the user device 104*a* of the user 102*a*. The control pattern creation engine 218 may be configured to create the control pattern by encrypting the interactive information and/or the gesture input. As explained above, the control pattern creation engine 218 determines the vibrotactile output for the control pattern by adjusting the parameters such as, the timing and the intensity of the vibrotactile output in order to control the adult toy 106*b* of the user 102*b*. Thereafter, the control pattern is transmitted by the server system 200 to the user device 104*b* of the user 102*b*.

The combining engine 220 includes a suitable logic and/or interfaces for combining one or more control patterns received from a user, such as the user 102*a*. The user 102*a* may provide inputs related to sequence, and playback speed associated with each control pattern of the one or more control patterns in the interactive application 110 which will be explained with reference to FIGS. 7A, and 7B. As such, the combining engine 220 is configured to create a new control pattern by combining the one or more control patterns received from the user 102*a* based at least on the sequence of the each control pattern. The new control pattern may be used by the user 102*a* for operating the adult toy 106*a* or may be transmitted to the user 102*b* in order to operate the adult toy 106*b*.

As explained above, the control pattern created by each user 102*a*-102*n* may be stored in the database 204 and is made available in the application 110, thus enabling the users 102 to access each other's control pattern for experiencing the sexual stimulation by operating their corresponding adult toys in the control pattern's way. The user accessing the control pattern of another user can understand the interactive information encrypted in the control pattern by sensing the vibrotactile output. The user may transmit the decrypted information upon sensing the vibrotactile output, to the server system 200. As such, the validation engine 222 may validate the decrypted information for enabling a connection between two users in the application, if the decrypted information matches with the user inputs of the other user.

Figure 3:
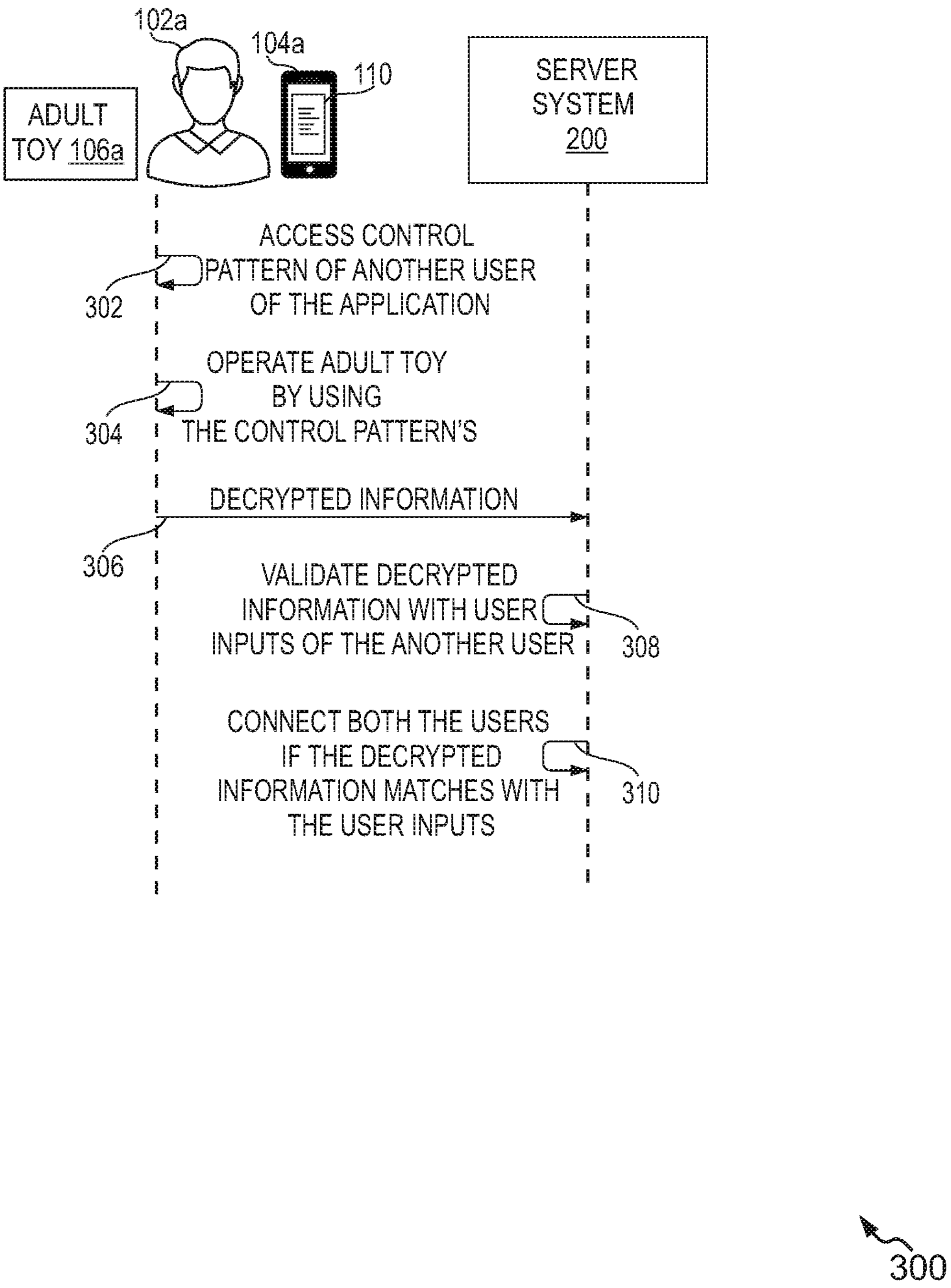
FIG. 3 illustrates a sequence flow diagram representation for enabling connection between two users in interactive application, in accordance with an example embodiment of the present disclosure.

Referring to FIG. 3 in conjunction with FIG. 2, a sequence flow diagram 300 for enabling connection between two users in the application is shown in accordance with an example embodiment of the present disclosure. At 302, a user, such as the user 102*a* with the user device 104*a* accesses the control pattern of another user, such as the user 102*b* made available in the application 110. At 304, the user 102*a* operates the adult toy 106*a* by using the control pattern of the user 102_b_. This enables the user 102_a_ to understand the interactive information and/or the encrypted information of the control pattern associated with the user 102_b_ based on the sexual stimulation caused by the vibrotactile output of the adult toy 106_a_ when the adult toy 106_a_ is operated by using the control pattern of the user 102_b_.

At 306, the user 102_a_ sends a decrypted information to the server system 200, upon experiencing the sexual stimulation caused by the adult toy 106_b_ by using the control pattern associated with the user 102_b_. The decrypted information provided by the user 102_a_ may be in form of the text input, the audio input, or the gesture input, as these are the types of user inputs provided by the user while creating the control pattern.

At 308, the server system 200 is configured to validate the decrypted information received by the user 102_a_ with the user inputs of the user 102_b_ provided in the interactive application 110 while creating the control pattern. More specifically, the validation engine 222 with access to the database 204 or 114, is configured to compare the decrypted information received from the user 102_a_ with the interactive information or the user inputs provided by the user 102_b_ in the application 110, while creating the control pattern.

At 310, the server system 200 facilitates connection between the user 102_a_ and the user 102_b_ as friends in the interactive application 110, if the decrypted information received from the user 102_a_ matches with the user inputs provided by the user 102_b_. In other words, the server system 200 connects both the users (e.g., the users 102_a_ and 102_b_) as friends in the application 110, if the user 102_a_ can recognize the user inputs of the user 102_b_ by feeling the vibrotactile output of the adult toy 106_a_. Further, the server system 200 may send a notification to the users 102_a_ and 102_b_ indicative of connection of the users 102_a_ and 102_b_ as friends in the application 110. Similarly, any user using the application 110 may be automatically connected as friends in the application 110 by recognizing the control pattern of the other user.

Figure 4:
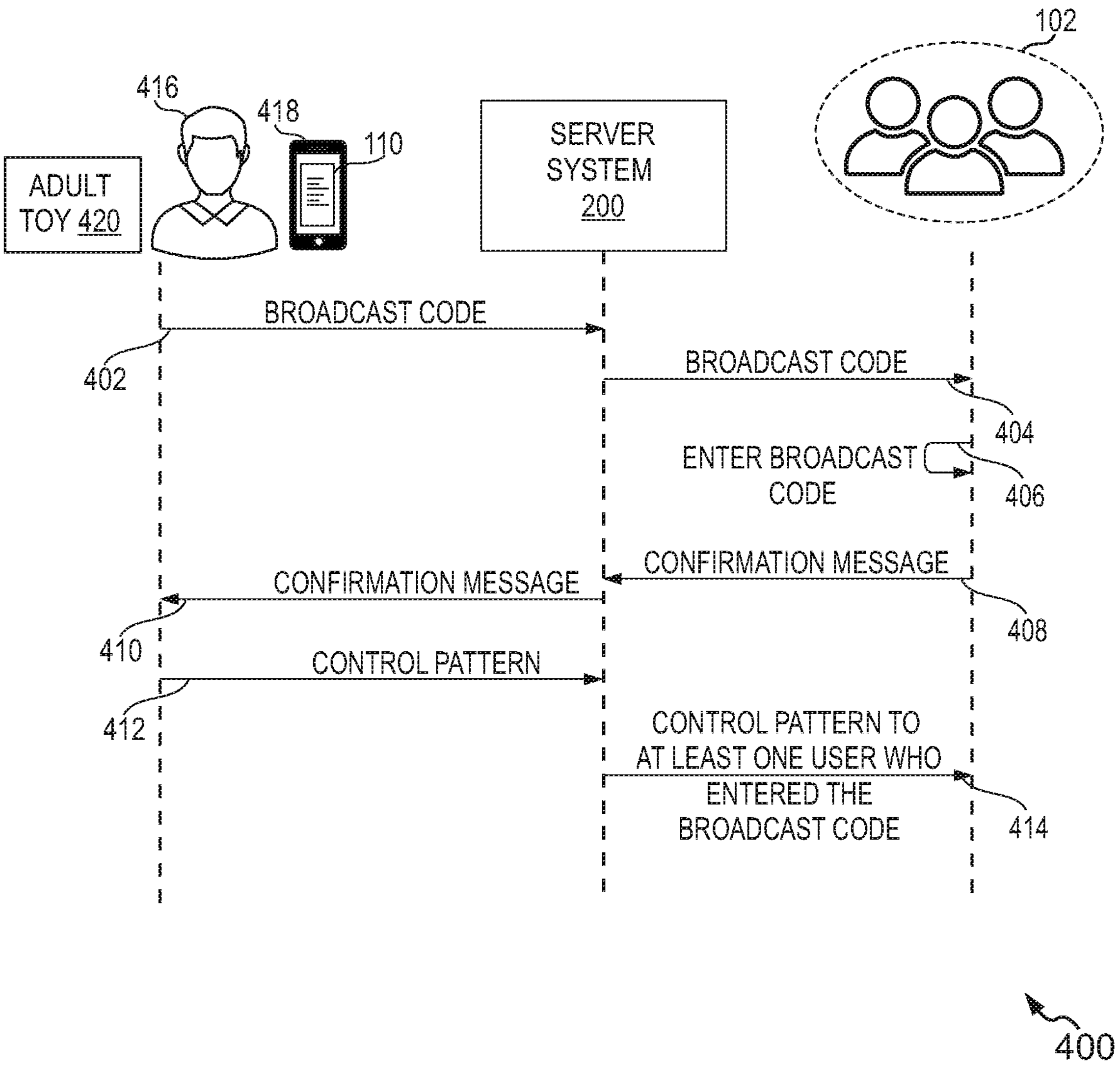
FIG. 4 illustrates a sequence flow diagram representation for enabling the adult toys of the users to vibrate along with the adult toy of a broadcast host, in accordance with an example embodiment of the present disclosure.

Referring now to FIG. 4 in conjunction with FIG. 2, a sequence flow diagram 400 for online broadcasting for enabling the adult toys of the users to vibrate along with the adult toy of a broadcast host is shown in accordance with an example embodiment of the present disclosure. At 402, a broadcast host 416 of the interactive application 110 sends a broadcast code to the server system 200 for initiating a broadcasting show. More specifically, the broadcast code may be shared by the broadcast host 416 by accessing the application 110 installed in a user device 418 associated with the broadcast host 416. The broadcasting show enables the users 102 associated with their respective adult toys 106_a_-106_n_ to vibrate with the hosts' adult toy (such as, an adult toy 420) in the same way.

At 404, the server system 200 transmits the broadcast code received from the broadcast host 416 to the users 102 of the interactive application 110. At 406, the users 102 who want to join the broadcasting show enter the broadcast code in the application 110. More specifically, at least one user of the users 102 may enter the broadcast code in the application 110 for joining the broadcasting show. For instance, the broadcast code is sent to all the users 102_a_-102_n_ by the server system 200, and only the users 102_a_-102_c_ may enter the broadcast code in the application 110. Thus, the users 102_a_-102_c_ are allowed to join the broadcasting show and vibrate their respective adult toys 106_a_-106_c_ along with the adult toy 420 of the broadcast host 416.

In one scenario, the broadcast code may be a QR code. In this scenario, upon clicking on the QR code in the application 110, the user (e.g., the user 102_a_) may be redirected to an external application that is installed in the user device 104_a_ to scan the QR code. Thereupon, the information associated with the broadcast host 416 is entered in the application 110 of the user device 104_a_ for joining the broadcasting show. In another scenario, the broadcast code may be an alphanumeric code. In this scenario, the user 102_a_ may enter the alphanumeric code in a data field provided in the application 110 for joining the broadcasting show with the broadcast host 416.

At 408, the application 110 sends a confirmation message by the at least one user indicative of approval for joining the broadcasting show to the server system 200. At 410, the server system 200 transmits the confirmation message to the broadcast host 416. At 412, the broadcast host 416 sends a control pattern created by the broadcast host to the server system 200. At 414, the server system 200 transmits the control pattern associated with the broadcast host 416 to the at least one user (e.g., the users 102_a_-102_c_) who entered the broadcast code for joining the broadcasting show. This enables the users 102_a_-102_c_ associated with their respective adult toys 106_a_-106_c_ to vibrate in the same way as that of the adult toy 420 associated with the broadcast host 416 (i.e. according to the vibrotactile output associated with the control pattern of the broadcast host 416) during the broadcasting show.

FIGS. 5A, 5B, 5C, and 5D collectively, represent example representation of user interfaces (UIs) displayed to the user for receiving user inputs from the user, in accordance with an embodiment of the present disclosure.

Figure 5A:
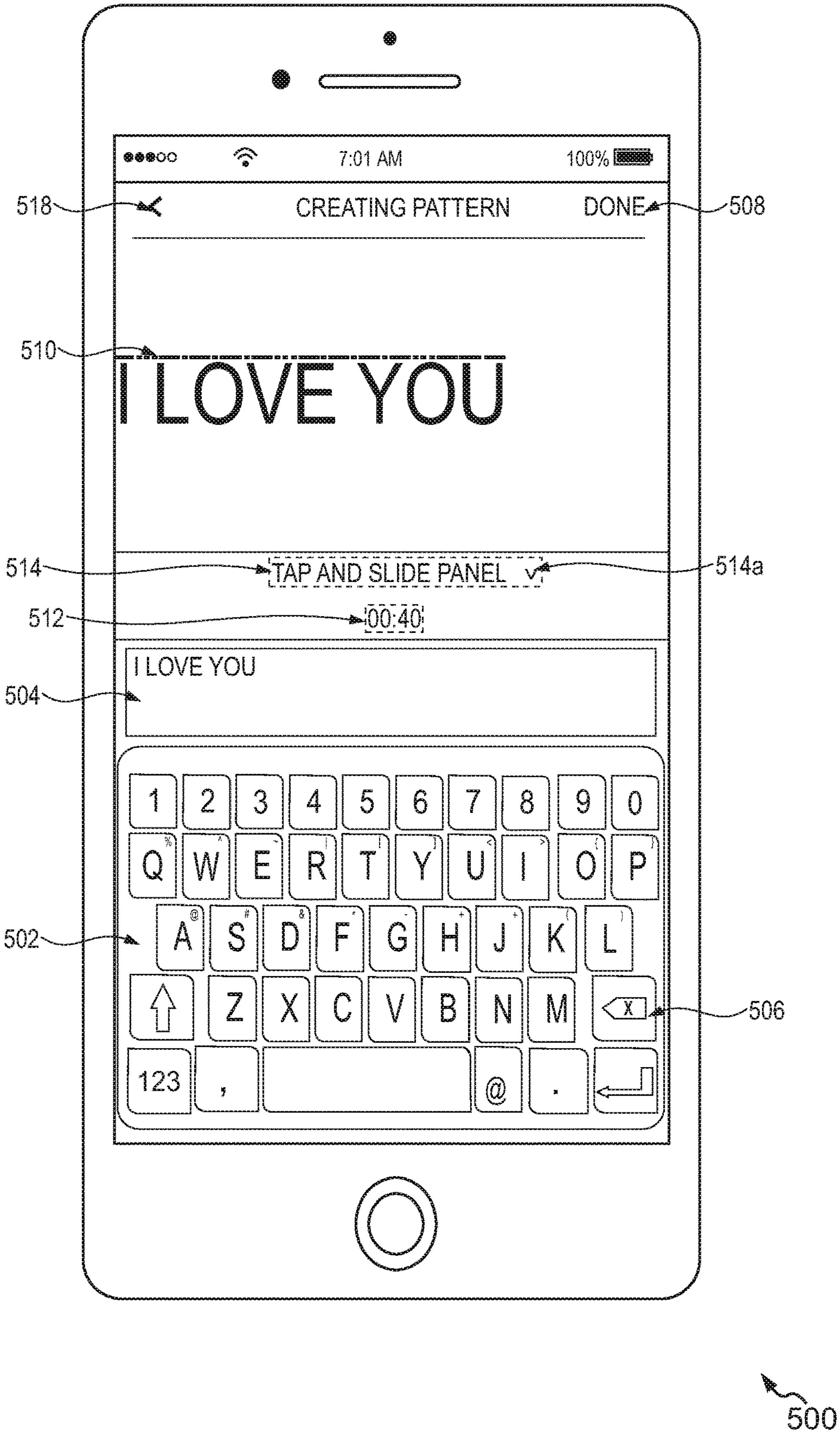
FIGS. 5A, 5B, 5C, and 5D, collectively, represent example representation of user interfaces (UIs) displayed to the user of the interactive application for receiving user inputs, in accordance with an embodiment of the present disclosure.

As shown in FIG. 5A, a representation of a user interface (UI) 500 is displayed to a user, such as the user 102_a_ for receiving a text input is shown in accordance with an embodiment of the present disclosure. The UI 500 renders an alphanumeric keyboard 502 and an input field 504. The user 102_a_ uses the alphanumeric keyboard 502 rendered in UI 500 for providing the user input (i.e. the text input). The user 102_a_ may provide a touch input or a gesture input on the alphanumeric keyboard 502 for entering the text input. The text input provided by the user 102_a_ by using the alphanumeric keyboard 502 is simultaneously depicted in the input field 504 (exemplary depicted to be 'I LOVE YOU'). The user 102_a_ may use a button 506 rendered in the UI 500 for editing the sentence of the text input. More specifically, upon invoking the button 506, a letter in the sentence (i.e. the text input) will be deleted.

Upon creating the text input, the user 102_a_ provides an input on a button 508 associated with the text "DONE". Based on user input on the button 508, the text input is transmitted to the server system 200 through the application 110. The server system 200 managing the application 110 is configured to analyze the text input and convert the text input into the control pattern by encrypting the text input. Further, the server system 200 adjusts the timing and intensity of the vibrotactile output for the control pattern as explained above. For example, the text input may be converted to the control pattern, such as a control pattern 510 by using the Morse code. The server system 200 managing the application 110 is further configured to render the control pattern 510 along with the text input in the UI 500. Further, the user 102_a_ may upload the control pattern 510 in the application 110, which enables the control pattern 510 to be accessible by other users, such as the users 102_b_-102_n_ of the application 110 as explained above.

Additionally, the UI 500 depicts an information field 512 for depicting the timing (exemplary depicted to be 00:40) of the vibrotactile output associated with the control pattern 510. In this example, the timing of the vibrotactile output associated with the control pattern 510 is 40 seconds. In other words, the timing of the vibrotactile output for the text input "I LOVE YOU" is 40 seconds.

Figure 5B:
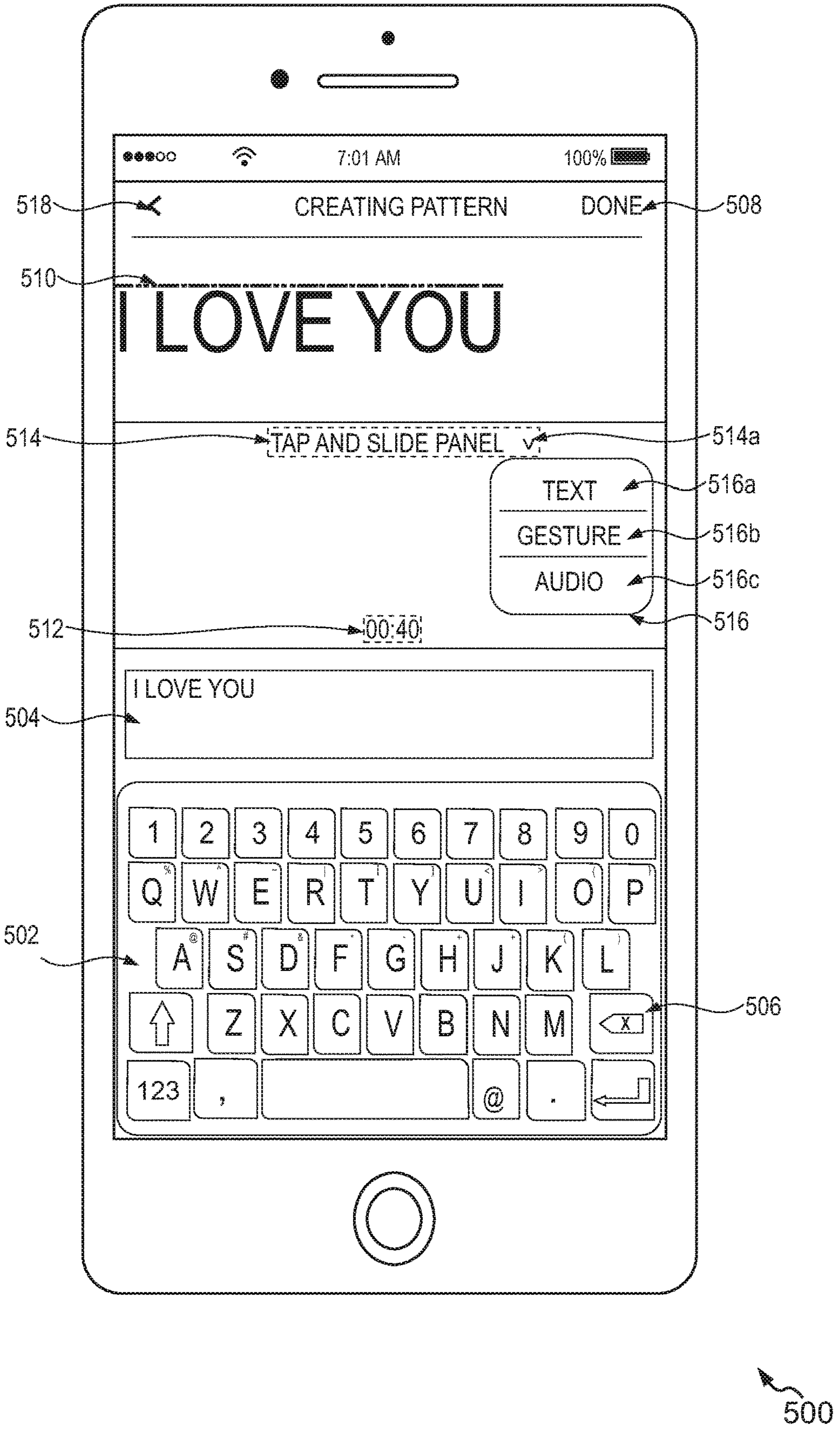

Further, the UI 500 depicts an option 514 associated with the text "TAP AND SLIDE PANEL". The option 514 is associated with a drop down menu 514*a*. Upon selection of the drop down menu 514*a* by the user 102*a*, a drop down list 516 is rendered in the UI 500 for depicting a list of options, such as an option 516*a*, an option 516*b*, and an option 516*c* (as shown in FIG. 5B). The options 516*a*, 516*b* and 516*c* are associated with the text "TEXT", "GESTURE", and "AUDIO", respectively. It should be understood that the UI 500 is rendered based on the user selection of the option 516*a*. Further, the user 102*a* may be redirected to a Homepage (not shown in Figures) of the application 110 based on the selection of a button 518 rendered on the UI 500.

Figure 5C:
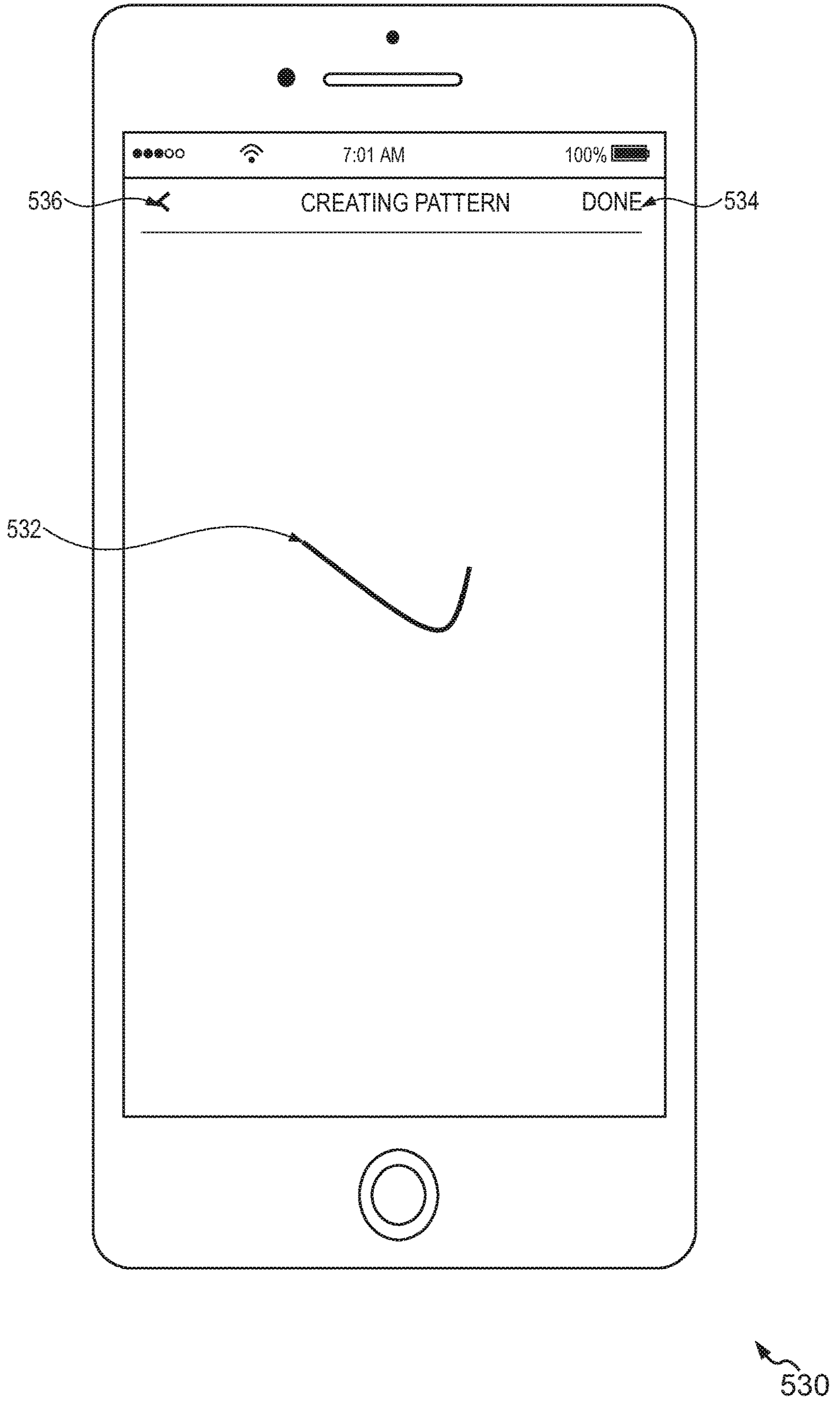

The user 102*a* may be rendered with an UI 530 based on user selection of the option 516*b* for receiving the gesture input 532 from the user 102*a* (as shown in FIG. 5C). Upon providing the gesture input, the user 102*a* may use a button 534 for transmitting the gesture input 532 to the server system 200 for creating the control pattern. The user 102*a* may be redirected to the UI 500 based on the selection of a button 536 rendered on the UI 530. In an embodiment, the UI 530 may be rendered with the option, such as the option 514 for enabling the user to switch to the UI 500.

Figure 5D:
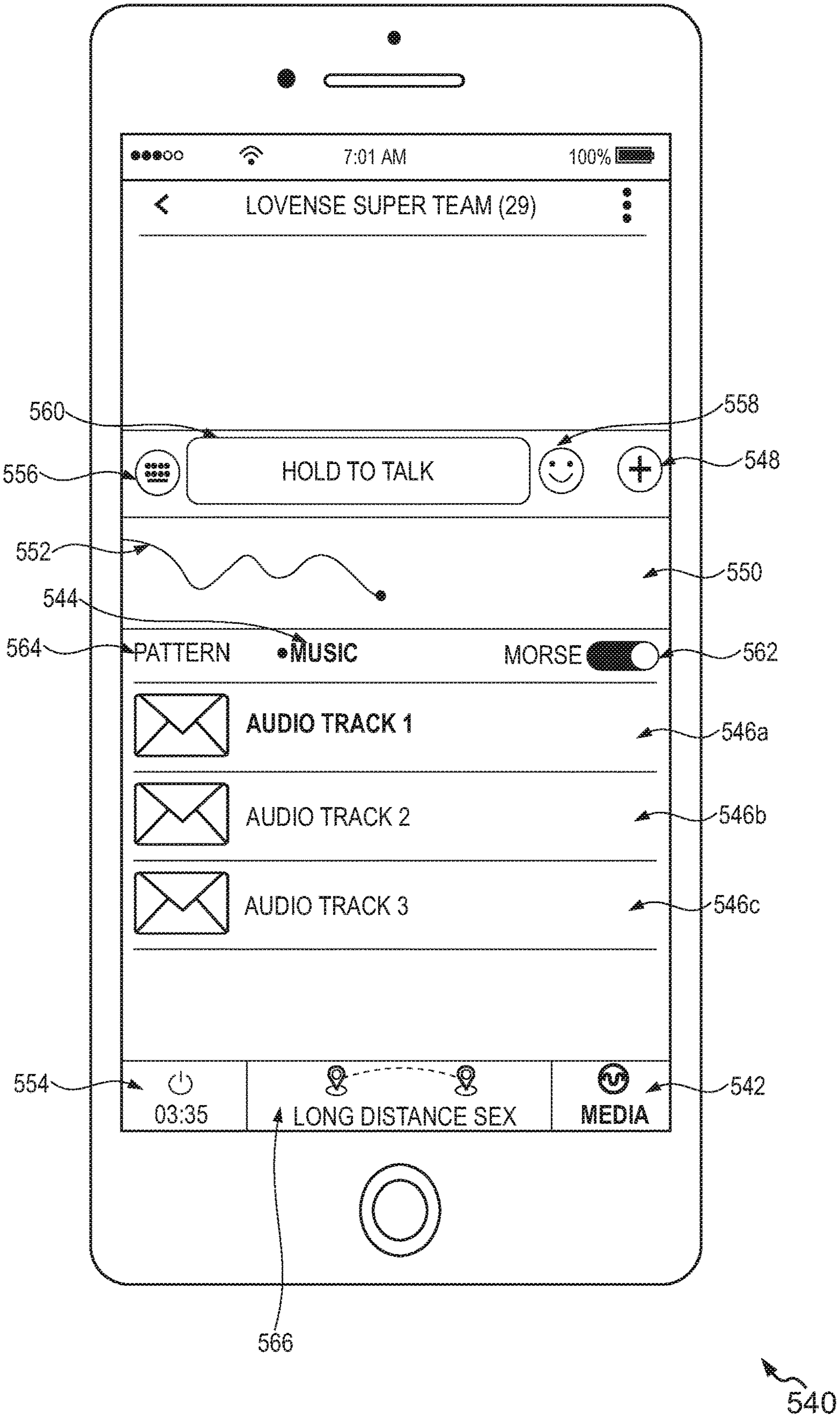

Referring to FIG. 5D, a representation of a UI 540 displayed to a user, such as the user 102*a* for receiving the audio input is shown in accordance with an embodiment of the present disclosure. The UI 540 is rendered by the application 110 on the user device 104*a* based on user selection of the option 516*c* in the UI 500. The UI 540 is depicted to include an icon 542 associated with the text "MEDIA" that indicates the type of input as the audio input in the UI 540. For illustrative purpose, the icon 542 in the UI 540 is exemplary highlighted by bold to indicate the type of input in the UI 540.

The UI 540 is depicted to include an option 544 associated with the text "MUSIC". The UI 540 depicts one or more audio tracks, such as an audio track 546*a*, an audio track 546*b*, and an audio track 546*c* based on the user selection of the option 544. The audio tracks 546*a*-546*c* may be predefined and/or default audio tracks provided by the application 110. In an embodiment, the user 102*a* may select an audio track from the local repository of the user device 104*a* and/or download other audio tracks from the application 110 by invoking a button 548. The UI 540 is depicted to include a sound wave field 550. Upon selecting an audio track (e.g., the audio track 546*a*), a sound wave 552 associated with the audio track 546*a* is depicted in the sound wave field 550, while the audio track 546*a* is played in the application 110. The sound wave field 550 enables the user 102*a* to analyze the volume and/or amplitude of the audio track 546*a* while playing. For illustrative purposes, the audio track 546*a* and the option 544 that are selected by the user 102*a* are exemplarily highlighted by bold for indicating the selection in the UI 540. Further, the user 102*a* may provide an input on an actionable icon 554 to stop playing the audio track 546*a*. Additionally, the actionable icon 554 is associated with a time length (exemplary depicted to be 03:25) which corresponds to the time length of the audio track 546*a* that is already played. Thus, based on the time length information, the user 102*a* may stop the audio track 546*a* by providing input on the actionable icon 554. In one scenario, the audio track 546*a* may be transmitted to the server system 200 to create the control pattern by analyzing the volume of the audio track 546*a* as explained above. In another scenario, the audio track 546*a* is already played until a specified time length may be sent to the server system 200 for creating the control pattern.

The UI 540 is further depicted to include a button 556, and a button 558. The UI 540 may be rendered with a pop-up keyboard (not shown in Figures) upon providing input on the button 556 by the user 102*a*. As such, the user 102*a* may use the pop-up keyboard for providing inputs and/or searching the audio tracks in the application 110. Further, the UI 540 may be rendered with a pop-up emoji section (not shown in Figures) for user selection based on the user input on the button 558. In one embodiment, the user 102*a* may be redirected to the UI 500 based on user input on the button 556.

The UI 540 depicts an option 560 associated with the text "HOLD TO TALK". The user 102*a* selects and/or holds the option 560 for recording a voice message in order to provide the audio input to the server system 200. The UI 540 further depicts a toggle switch 562 associated with the text "MORSE". Prior to recording the voice message, the user 102*a* may provide input on the toggle switch 562. As such, the server system 200 receiving the audio input in form of a recorded voice message from the user 102*a* converts the recorded voice message to the text format based on user input on the toggle switch 562. Further, the text format of the audio input is utilized by the server system 200 to create the control pattern as explained above. In an embodiment, the server system 200 may analyze the volume associated with the recorded voice message for creating the control pattern. In another embodiment, the server system may convert the audio track, such as the audio track 546*a* to the text format for creating the control pattern.

Further, the UI 540 depicts an option 564 associated with the text "PATTERN". The user 102*a* may be redirected to a UI (not shown in Figures) that depicts the control patterns created by providing either the text input, the audio input, or the gesture input based on user selection of the option 564. The UI 540 is depicted to include an actionable icon 566 associated with the text "LONG DISTANCE SEX". The user 102*a* may be redirected to a UI (not shown in Figures) that depicts a list of users, such as the users 102*b*-102*n* of the application 110. The user 102*a* may send the control pattern created by providing either the text input, the gesture input or the audio input as explained with reference to FIGS. 5A-5D, to the users 102*b*-102*n* of the application 110.

FIGS. 6A, 6B, 6C, and 6D collectively, represent example representation of user interfaces (UIs) displayed to the user for making friends in the application 110, in accordance with an embodiment of the present disclosure.

Figure 6A:
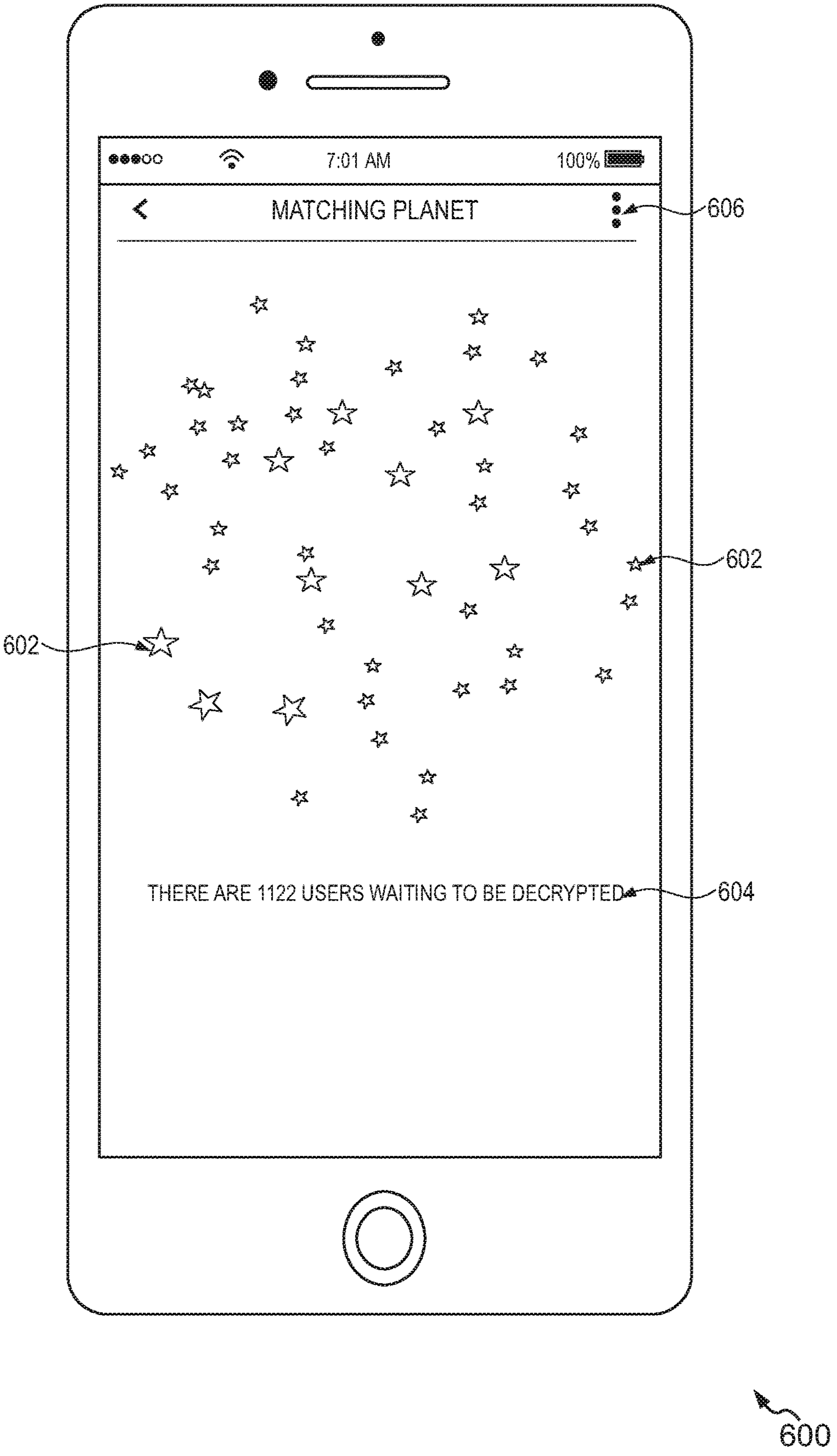
FIGS. 6A, 6B, 6C, and 6D, collectively, represent example representation of UIs displayed to the user for making friends in the application, in accordance with an embodiment of the present disclosure.
Figure 6B:
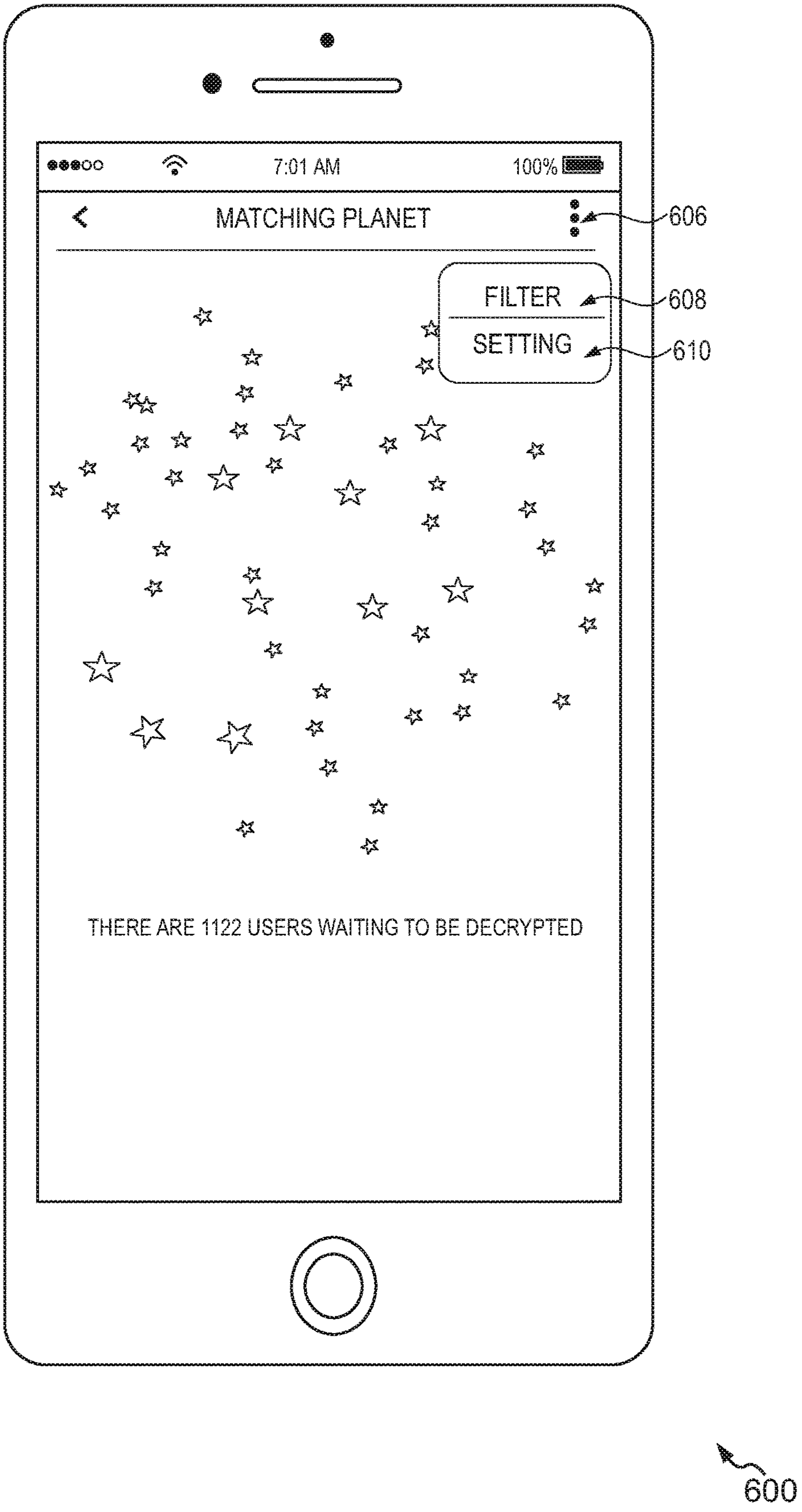

As shown in FIG. 6A, a representation of a UI 600 is displayed to a user, such as the user 102*a*. The UI 600 is depicted to include the control patterns 602 of the users 102 (exemplary depicted as stars) in the application 110. Further, the UI 600 is depicted to include an information field 604 for depicting number of control patterns (exemplary depicted to be "THERE ARE 1122 USERS WAITING TO BE DECRYPTED") made available to the user 102*a*. The user 102*a* may select one control pattern from the 1122 control patterns in the application 110. For instance, the user 102*a* may select a control pattern of other user (e.g., the user 102*b*) of the application 110. Upon selecting the control pattern associated with the user 102*b*, the user 102*a* is redirected to a UI 620 which will be explained with reference to FIG. 6D.

Figure 6C:
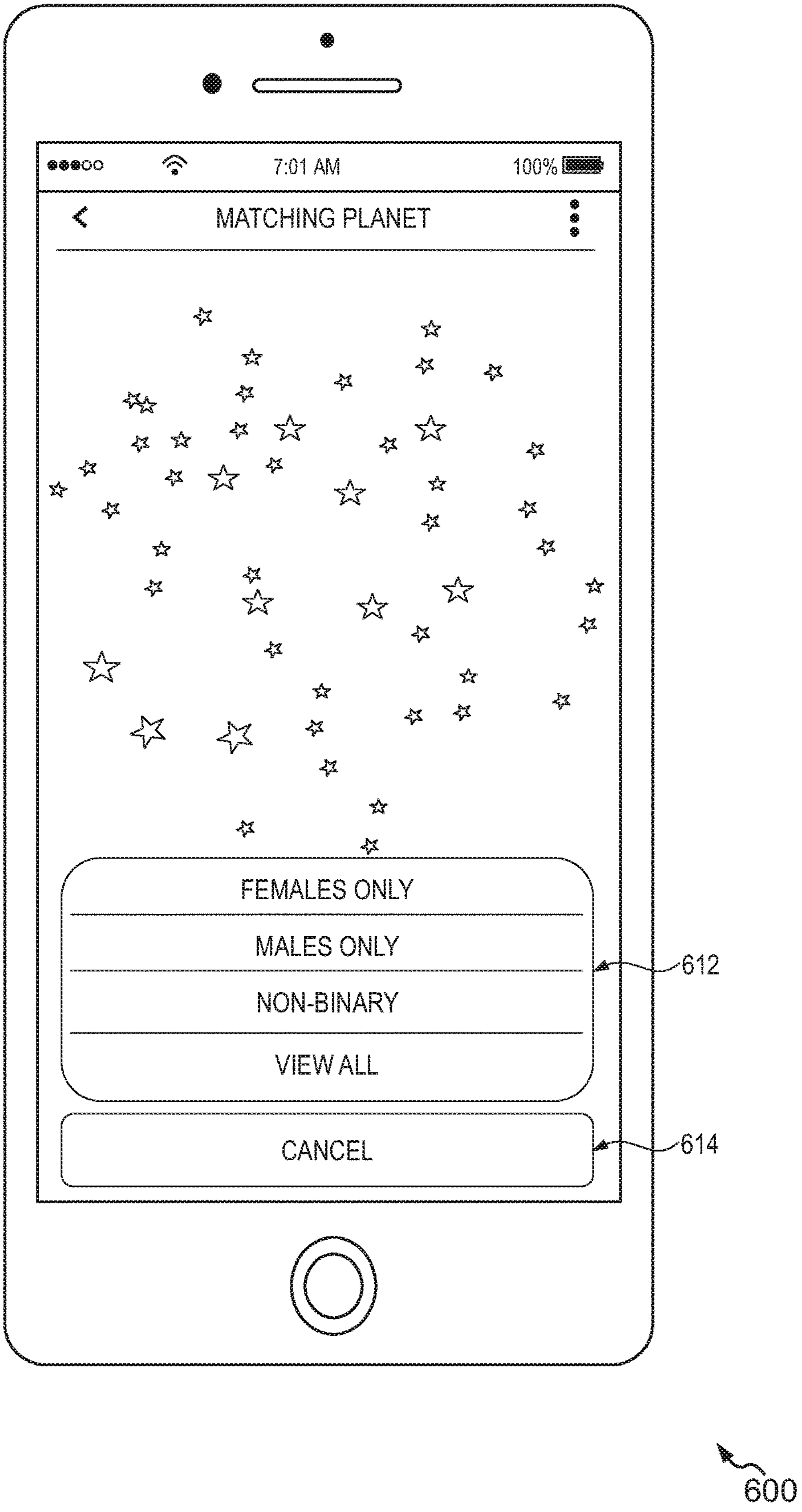

Further, the user 102*a* may provide inputs related to sexuality type for selecting a certain group of users from the users 102 by providing input on a button 606. Based on the user input, the UI 600 is rendered with a list providing an option 608 and an option 610. The options 608 and 610 are associated with text "FILTER", and "SETTING", respectively. Based on user selection of the option 608, the user 102*a* is rendered with a list 612 depicting the sexuality types (as shown in FIG. 6C). The list 612 including the sexuality types is exemplarily depicted to be "FEMALES ONLY", "MALES ONLY", "NON-BINARY, and "VIEW ALL" (as shown in FIG. 6C). The user 102*a* may select one or more sexuality types from the list 612. As a result, the UI 600 will depict the control pattern of the users of the application 110 based on the user selection of the sexuality type from the list 612. More specifically, server system 200 is configured to check and/or filter the users 102 of the application 110 based on the sexuality type provided by the user 102*a*, and display the control pattern of the one or more users (e.g., the users 102*b*, and 102*c*) based at least, in part on, the sexuality type. For instance, the user 102*a* may be a male who is interested in females. In this scenario, the user 102*a* may select the female option from the list 612. Thus, the control pattern of only the female users who are interested in male may be depicted to the user 102*a*. It is evident that the setting related to visibility of the control pattern of a user to other users of the application 110 can be adjusted in the application 110. Further, the UI 600 is depicted to include a button 614 associated with the text "CANCEL". The user 102*a* may provide input on the button 614 to cancel the filter setting associated with the sexuality type.

As explained above, each user of the application 110 can set the visibility of the control pattern to other users of the application 110. To that effect, a user (e.g., the user 102*a*) may provide input on the option 610 for setting the visibility of the control pattern to other users of the application 110. Upon providing input on the option 610, the user 102*a* may be provided with a list, such as the list 612 for selecting the sexuality type. Thus, the control pattern associated with the user 102*a* is made visible for the users of the sexuality type selected by the user 102*a*. In this scenario, server system 200 with the visibility setting associated with the user 102*a* displays the control pattern to the other users, such as the users 102*b*-102*n* of the application 110 based on the sexuality type provided by the user 102*a*. For instance, the user 102*a* may be a male who is interested in females. In this scenario, the user 102*a* may select female option from the list 612. Thus, the control pattern of the user 102*a* is made visible to only the female users of the application 110.

Figure 6D:
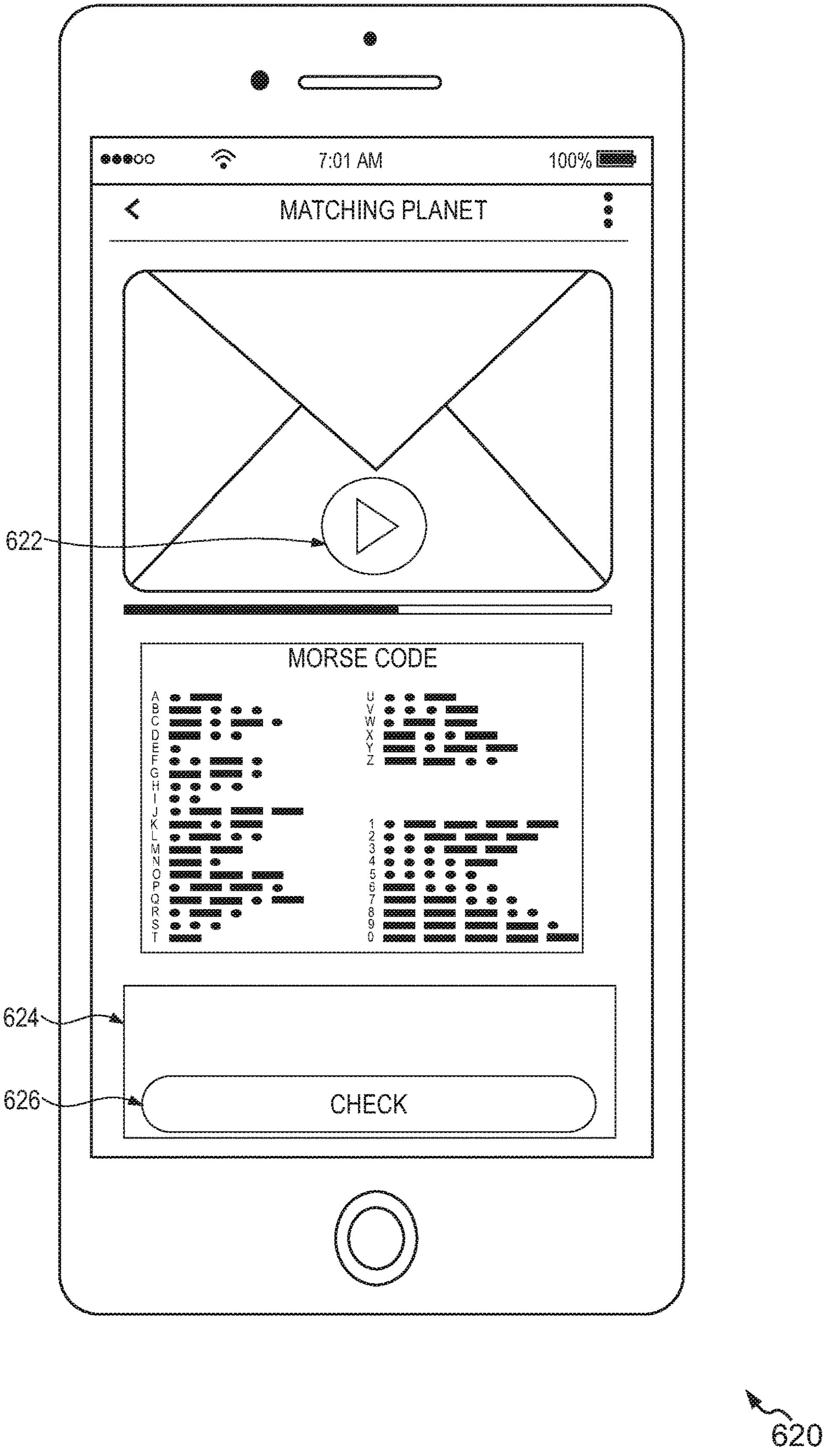

Referring to FIG. 6D, the UI 620 is depicted to include the selected control pattern (e.g., the control pattern of the user 102*b*) associated with a button 622. The user 102*a* can operate the adult toy 106*a* with the control pattern of the user 102*b* by providing input on the button 622. The user 102*a* can understand the interactive information encrypted in the control pattern of the user 102*b* by sensing the vibrotactile output provided by the adult toy 106*a* as explained above. Upon decrypting the interactive information associated with the control pattern of the user 102*b*, the user 102*a* may provide the decrypted information in a data field 624. Thereafter, the user 102*a* may check the decrypted information by providing the input on a button 626 associated with the text "CHECK". More specifically, the server system 200 may validate the decrypted information with the user input of the user 102*b* provided in the application 110 while creating the control pattern based on the user input on the button 626. Thereafter, the server system 200 automatically connects the user 102*a* and the user 102*b* as friends in the application 110, if the decrypted information matches with the user inputs of the user 102*b*.

Figure 7A:
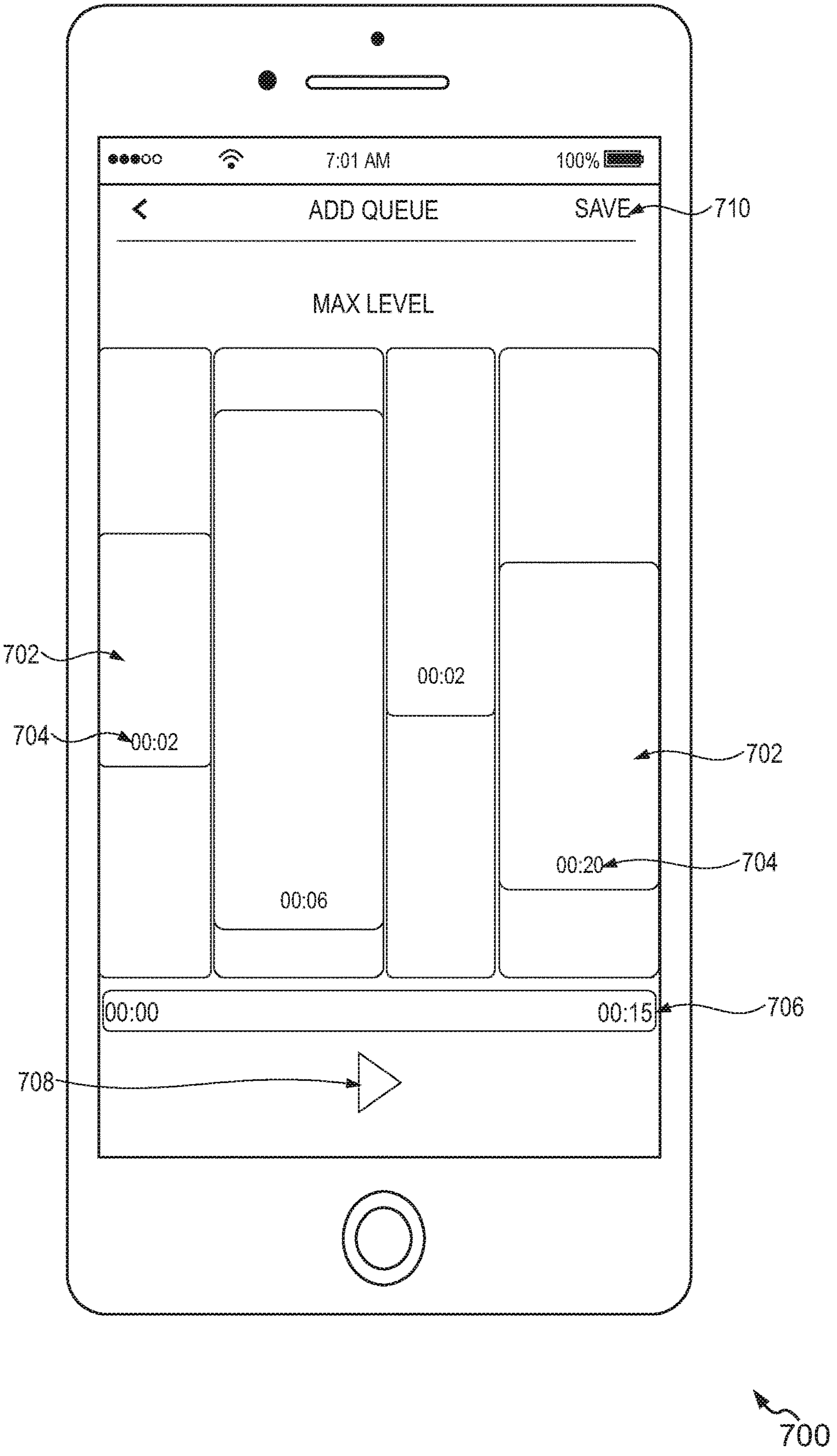
FIGS. 7A and 7B, collectively, represent example representation of UIs displayed to the user for combining one or more control patterns in the interactive application, in accordance with an embodiment of the present disclosure.
Figure 7B:
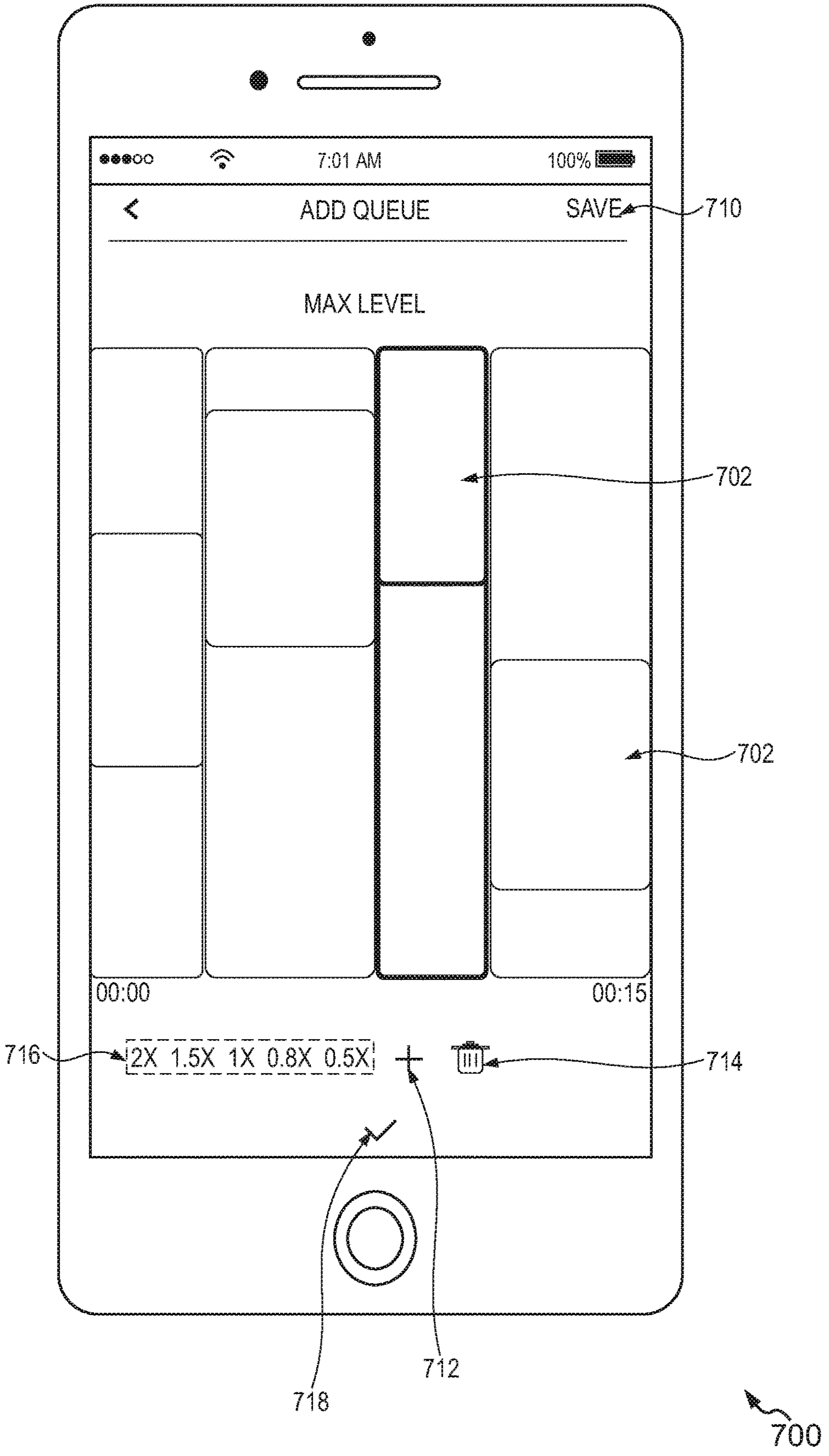

FIGS. 7A, and 7B collectively, represent example representation of user interfaces (UIs) displayed to the user for combining one or more control patterns in the application 110, in accordance with an embodiment of the present disclosure. As shown in FIG. 7A, each control pattern of the one or more control patterns 702 associated with a user, such as the user 102*a* is exemplarily depicted as a rectangular block in the UI 700. The user 102*a* may adjust a sequence of the each control pattern by selecting the each control pattern priority wise in the application 110. Further, the user 102*a* may provide inputs in the UI 700 for interchanging the sequence of the control patterns 702. The UI 700 is depicted to include a time period 704 of the each control pattern. Additionally, the UI 700 depicts a total time length 706 of the pattern created by combining the control patterns 702. The user 102*a* may operate the adult toy 106*a* in the new control pattern's way by providing user input on an actionable icon 708.

Further, the user 102*a* can remove any control pattern in the combination or add new control patterns into the combination pattern. Particularly, a control pattern may be selected by the user 102*a* (as shown in FIG. 7B). The selection of the control pattern in the UI 700 is exemplarily depicted with bold outer boundary. The user 102*a* may provide input on an actionable icon 712 for adding the new control patterns into the combination pattern, and provide input on an actionable icon 714 for deleting the selected control pattern from the combination pattern. The new pattern may be added to the right of the selected control pattern. Moreover, the playback speed of the control patterns 702 may vary between a maximum level and a minimum level by providing inputs in a playback speed section 716 (exemplary depicted to be 2×, 1.5×, etc.). The playback speed corresponds to the vibrating frequency or intensity of the vibration. For instance, if the playback speed is high, the frequency of vibrations and/or intensity of vibrotactile output produced by the adult toy is high. Upon adjusting the playback speed, and the sequence of the selected pattern, the user 102*a* may save the changes by using an actionable icon 718. Upon creating the new control pattern by combining the control patterns 702, the user 102*a* may provide user input on a button 710 associated with text "SAVE" for saving the new control pattern in the application 110.

Figure 8:
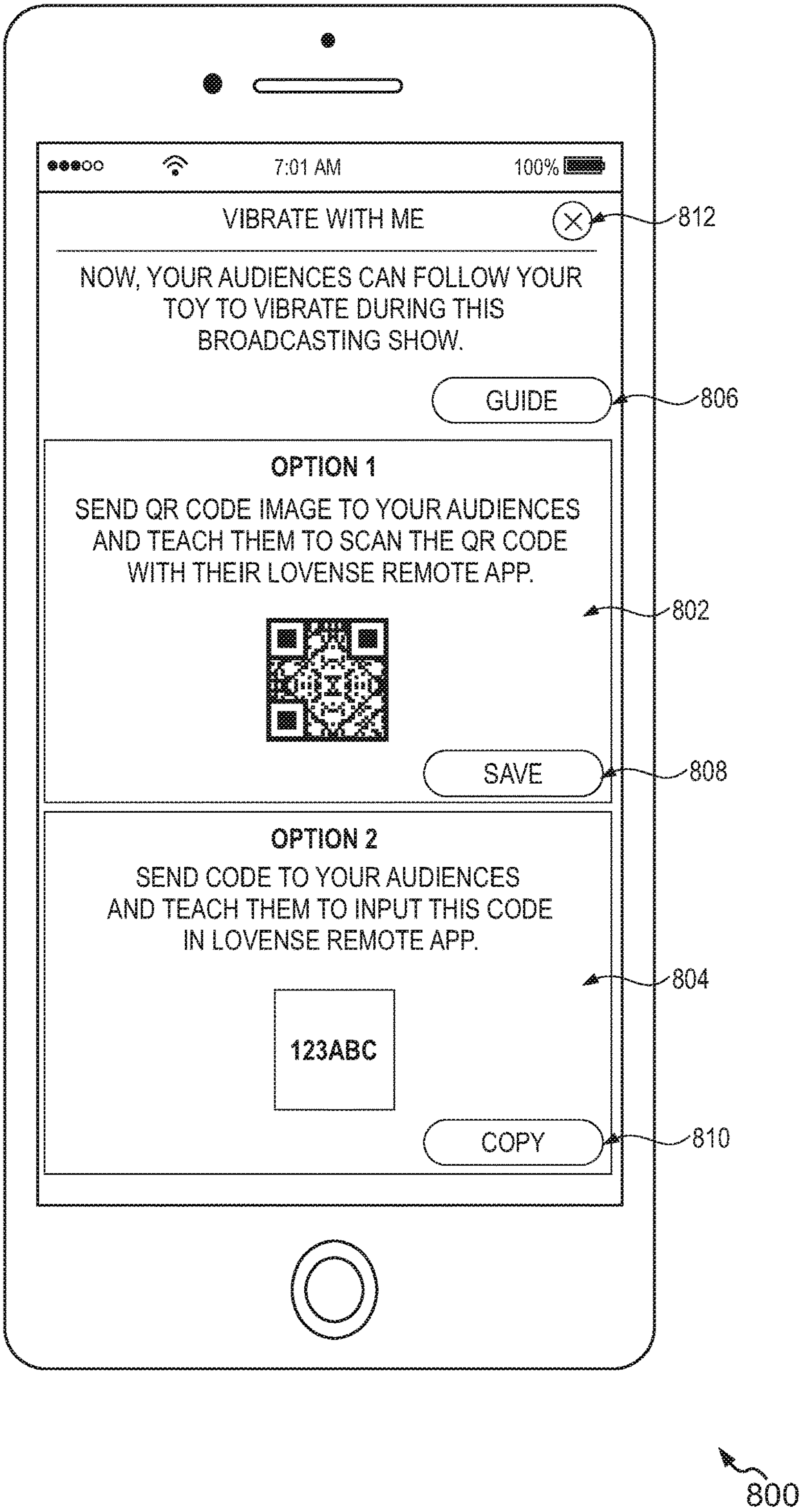
FIG. 8 illustrates an example representation of a UI displaying a broadcast code, in accordance with an embodiment of the present disclosure.

FIG. 8 illustrates an example representation of a UI 800 displaying a broadcast code, in accordance with an embodiment of the present disclosure. The UI 800 is depicted to the broadcast host 416, upon selecting an option (not shown in Figures) provided in the application 110 for creating the broadcasting show. The UI 800 depicts two options, such as an option 802, and an option 804 to the host 416 for selecting the type of broadcast code to be shared to the users 102. As shown in FIG. 8, the option 802, and the option 804 are exemplary depicted to include a quick response (QR) code, and an alphanumeric code, respectively. The host 416 may select either the option 802 for sharing the QR code or the option 804 for sharing the alphanumeric code to the users 102. Upon selecting either one option 802 or 804 depicted in the UI 800, the selected broadcast code is shared to the users 102 by providing input on a button 806 associated with the text "GUIDE".

Further, the UI 800 is depicted to include a button 808 for the option 802, and a button 810 for the option 804. The buttons 808 and 810 are associated with the text "SAVE", and "COPY", respectively. Upon receipt of the broadcast code in form of the QR code, the users (e.g., the users

102*a*-102*c*) who want to join the broadcasting show may provide input on the button 808 and save the QR code. Thereafter, the user 102*a* may scan the QR code by using one or more applications in the user device 104*a* for joining the broadcasting show. Further, upon receipt of the broadcast code in form of the alphanumeric code, the user 102*a* may copy the alphanumeric code by providing input on the button 810. Thereafter, the user 102*a* may paste and/or enter the alphanumeric code in respective data field (not shown in Figures) in the application 110 for joining the broadcasting show. The host 416 may be redirected to the Homepage (not shown in Figures) based on the input from the host 416 on a button 812 in the UI 800.

Figure 9:
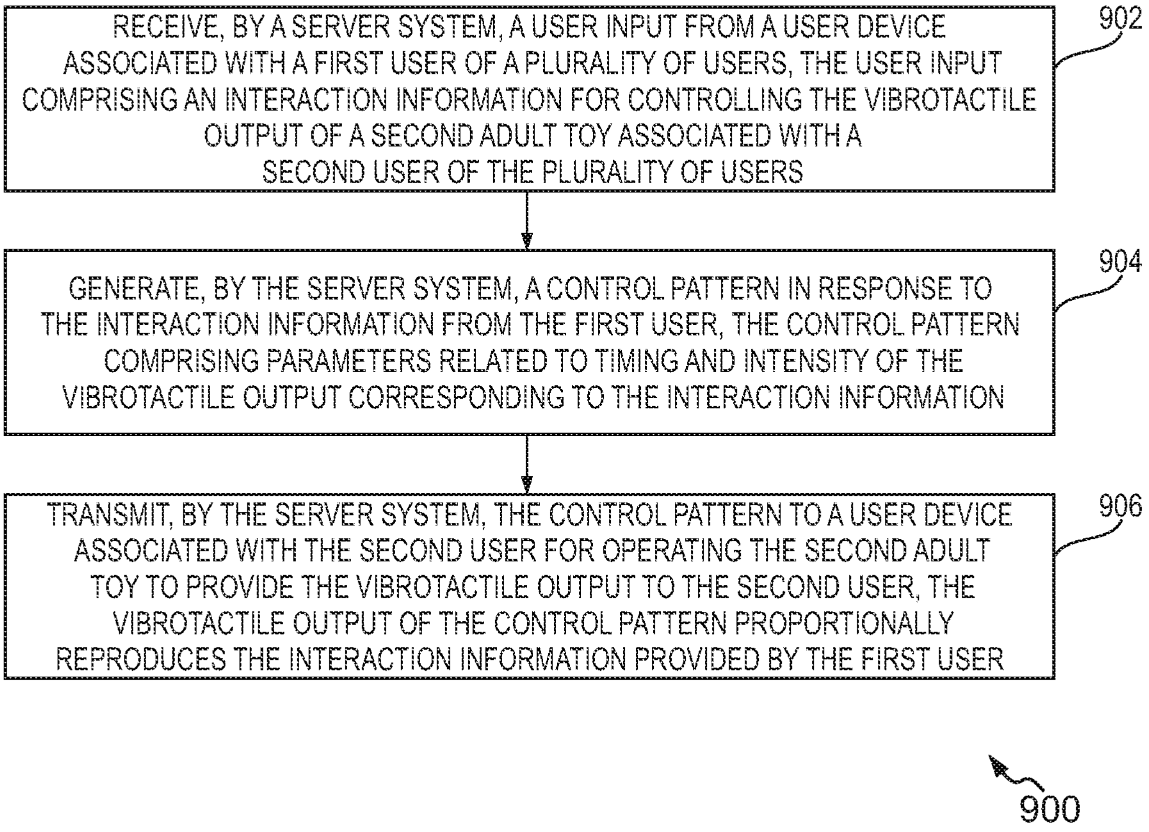
FIG. 9 illustrates a flow diagram of a method for controlling the vibrotactile output of the adult toys of the users, in accordance with an embodiment of the present disclosure.

FIG. 9 illustrates a flow diagram of a method 900 for controlling the vibrotactile output of the adult toys of the users located in remote locations, in accordance with an embodiment of the present disclosure. The method 900 depicted in the flow diagram may be executed by, for example, the server system 200. Operations of the flow diagram of method 900, and combinations of operation in the flow diagram of method 900, may be implemented by, for example, hardware, firmware, a processor, circuitry, and/or a different device associated with the execution of software that includes one or more computer program instructions. It is noted that the operations of the method 900 can be described and/or practiced by using a system other than these server systems. The method 900 starts at operation 902.

At operation 902, the method 900 includes receiving, by a server system, a user input from a user device associated with a first user of a plurality of users. The user input includes an interaction information for controlling the vibrotactile output of a second adult toy associated with a second user of the plurality of users. The interaction information includes at least one of a text input, an audio input, and a gesture input provided in an interactive application installed on the user device of the first user.

At operation 904, the method 900 includes generating, by the server system, a control pattern in response to the interaction information from the first user. The control pattern includes parameters related to timing and intensity of the vibrotactile output corresponding to the interaction information. In an embodiment, the server system 200 is configured to analyze the amplitude associated with the audio input. Further, the server system 200 creates the control pattern based at least on the amplitude of the audio input. In another embodiment, the server system 200 may convert the audio input to a text format. In this scenario, the server system 200 creates the control pattern based on the text format of the audio input.

At operation 906, the method 900 includes transmitting, by the server system, the control pattern to a user device associated with the second user for operating the second adult toy to provide the vibrotactile output to the second user. The vibrotactile output of the control pattern proportionally reproduces the interaction information provided by the first user.

In an embodiment, the method performed by the server system receives a decrypted information from the first user in response to sensing the vibrotactile output associated with a control pattern of the second user by using the first adult toy of the first user. Further, the server system validates the decrypted information with a user input of the second user provided in the interactive application while creating the control pattern. Thereafter, the server system enables connection between the first user and the second user of the plurality of users as friends in the interactive application, if the decrypted information received from the first user matches with the user input provided by the second user. Additionally, the server system may receive an input from the first user related to sexuality type. Upon receipt of the input, the server system filters one or more users from the plurality of users based on receipt of the input related to the sexuality type, and displays at the user device of the first user, the control pattern associated with the one or more users of the plurality of users based at least, in part on, the sexuality type. Furthermore, the server system may receive an input from the first user related to visibility of the control pattern associated with the first user to other users of the plurality of users of the interactive application. In this scenario, the server system displays at the user device of the first user, the control pattern associated with the first user to the other users of the plurality of users based at least, in part on, the input related to the visibility of the control pattern.

In another embodiment, the server system receives one or more control patterns from the first user of the plurality of users. Further, one or more parameters related to sequence, and playback speed associated with each control pattern of the one or more control patterns are adjusted by providing inputs in the interactive application by the first user. The server system creates a new control pattern by combining the one or more control patterns based at least, in part on, the sequence associated with the each control pattern of the one or more control patterns.

In another embodiment, the server system is configured to transmit a broadcast code (such as the QR code or the alphanumeric code) received from a broadcast host of the interactive application to the plurality of users. Further, the server system is configured to receive a confirmation message indicative of approval for broadcasting show from at least one user of the plurality of users based at least on entering the broadcast code by at least one user in the interactive application. The server system sends the confirmation message related to approval for the broadcasting show from at least one user to the broadcast host. Thereafter, the server system is configured to broadcast a control pattern received from the broadcast host to at least one user of the plurality of users for enabling the adult toy of at least one user to vibrate along with the adult toy associated with the broadcast host during the broadcasting show.

Figure 10:
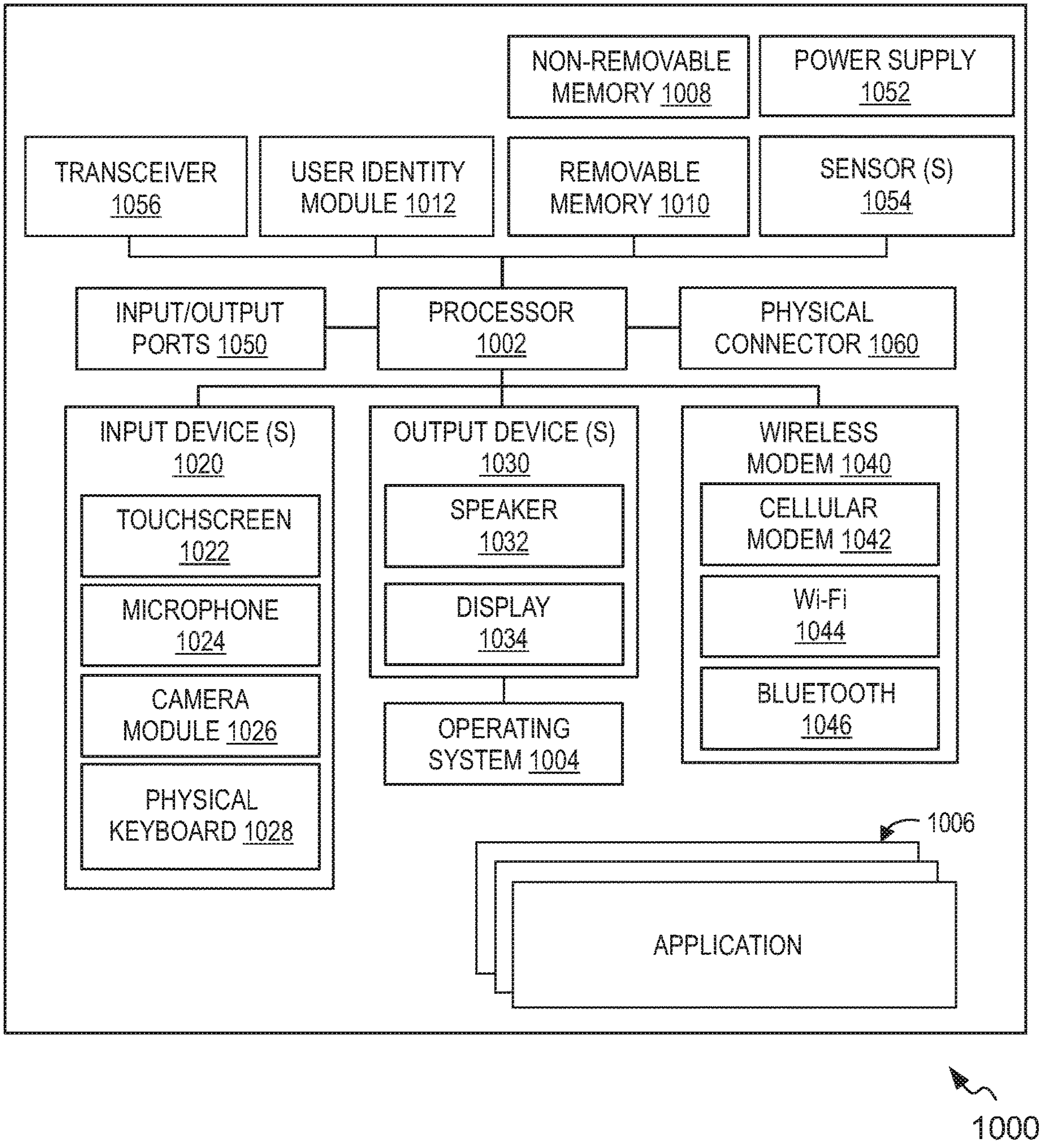
FIG. 10 is a simplified block diagram of an electronic device capable of implementing various embodiments of the present disclosure.

FIG. 10 is a simplified block diagram of an electronic device 1000 capable of implementing various embodiments of the present disclosure. For example, the electronic device 1000 may correspond to the user device 104*a*-104*n* of FIG. 1. The electronic device 1000 is depicted to include one or more applications 1006. For example, the one or more applications 1006 may include the application 110 of FIG. 1. The application 110 can be an instance of an application downloaded from the server system 200. One of the one or more applications 1006 installed on the electronic device 1000 are capable of communicating with a server system for controlling the vibrotactile output of the adult toys of the users.

It should be understood that the electronic device 1000 as illustrated and hereinafter described is merely illustrative of one type of device and should not be taken to limit the scope of the embodiments. As such, it should be appreciated that at least some of the components described below in connection with the electronic device 1000 may be optional and thus in an embodiment may include more, less or different components than those described in connection with the embodiment of the FIG. 10. As such, among other examples, the electronic device 1000 could be any of a mobile electronic device, for example, cellular phones, tablet computers, laptops, mobile computers, personal digital assistants (PDAs), mobile televisions, mobile digital assistants, or any combination of the aforementioned, and other types of communication or multimedia devices.

The illustrated electronic device 1000 includes a controller or a processor 1002 (e.g., a signal processor, microprocessor, ASIC, or other control and processing logic circuitry) for performing such tasks as signal coding, data processing, image processing, input/output processing, power control, and/or other functions. An operating system 1004 controls the allocation and usage of the components of the electronic device 1000 and supports for one or more operations of the application (see, the applications 1006), such as the application 110 that implements one or more of the innovative features described herein. In addition, the applications 1006 may include common mobile computing applications (e.g., telephony applications, email applications, calendars, contact managers, web browsers, messaging applications) or any other computing application.

The illustrated electronic device 1000 includes one or more memory components, for example, a non-removable memory 1008 and/or removable memory 1010. The non-removable memory 1008 and/or the removable memory 1010 may be collectively known as a database in an embodiment. The non-removable memory 1008 can include RAM, ROM, flash memory, a hard disk, or other well-known memory storage technologies. The removable memory 1010 can include flash memory, smart cards, or a Subscriber Identity Module (SIM). The one or more memory components can be used for storing data and/or code for running the operating system 1004 and the applications 1006. The electronic device 1000 may further include a user identity module (UIM) 1012. The UIM 1012 may be a memory device having a processor built in. The UIM 1012 may include, for example, a subscriber identity module (SIM), a universal integrated circuit card (UICC), a universal subscriber identity module (USIM), a removable user identity module (R-UIM), or any other smart card. The UIM 1012 typically stores information elements related to a mobile subscriber. The UIM 1012 in form of the SIM card is well known in Global System for Mobile (GSM) communication systems, Code Division Multiple Access (CDMA) systems, or with third-generation (3G) wireless communication protocols such as Universal Mobile Telecommunications System (UMTS), CDMA9000, wideband CDMA (WCDMA) and time division-synchronous CDMA (TD-SCDMA), or with fourth-generation (4G) wireless communication protocols such as LTE (Long-Term Evolution).

The electronic device 1000 can support one or more input devices 1020 and one or more output devices 1030. Examples of the input devices 1020 may include, but are not limited to, a touch screen/a display screen 1022 (e.g., capable of capturing finger tap inputs, finger gesture inputs, multi-finger tap inputs, multi-finger gesture inputs, or keystroke inputs from a virtual keyboard or keypad), a microphone 1024 (e.g., capable of capturing voice input), a camera module 1026 (e.g., capable of capturing still picture images and/or video images) and a physical keyboard 1028. Examples of the output devices 1030 may include, but are not limited to, a speaker 1032 and a display 1034. Other possible output devices can include piezoelectric or other haptic output devices. Some devices can serve more than one input/output function. For example, the touch screen 1022 and the display 1034 can be combined into a single input/output device.

A wireless modem 1040 can be coupled to one or more antennas (not shown in the FIG. 10) and can support two-way communications between the processor 1002 and external devices, as is well understood in the art. The wireless modem 1040 is shown generically and can include, for example, a cellular modem 1042 for communicating at long range with the mobile communication network, a Wi-Fi compatible modem 1044 for communicating at short range with an external Bluetooth-equipped device or a local wireless data network or router, and/or a Bluetooth-compatible modem 1046. The wireless modem 1040 is typically configured for communication with one or more cellular networks, such as a GSM network for data and voice communications within a single cellular network, between cellular networks, or between the electronic device 1000 and a public switched telephone network (PSTN).

The electronic device 1000 can further include one or more input/output ports 1050, a power supply 1052, one or more sensors 1054 for example, an accelerometer, a gyroscope, a compass, or an infrared proximity sensor for detecting the orientation or motion of the electronic device 1000 and biometric sensors for scanning biometric identity of an authorized user, a transceiver 1056 (for wirelessly transmitting analog or digital signals) and/or a physical connector 1060, which can be a USB port, IEEE 1294 (FireWire) port, and/or RS-232 port. The illustrated components are not required or all-inclusive, as any of the components shown can be deleted and other components can be added.

The disclosed method with reference to FIG. 9, or one or more operations of the server system 200 may be implemented using software including computer-executable instructions stored on one or more computer-readable media (e.g., non-transitory computer-readable media, such as one or more optical media discs, volatile memory components (e.g., DRAM or SRAM), or nonvolatile memory or storage components (e.g., hard drives or solid-state nonvolatile memory components, such as Flash memory components)) and executed on a computer (e.g., any suitable computer, such as a laptop computer, net book, Web book, tablet computing device, smart phone, or other mobile computing device). Such software may be executed, for example, on a single local computer or in a network environment (e.g., via the Internet, a wide-area network, a local-area network, a remote web-based server, a client-server network (such as a cloud computing network), or other such network) using one or more network computers. Additionally, any of the intermediate or final data created and used during implementation of the disclosed methods or systems may also be stored on one or more computer-readable media (e.g., non-transitory computer-readable media) and are considered to be within the scope of the disclosed technology. Furthermore, any of the software-based embodiments may be uploaded, downloaded, or remotely accessed through a suitable communication means. Such a suitable communication means includes, for example, the Internet, the World Wide Web, an intranet, software applications, cable (including fiber optic cable), magnetic communications, electromagnetic communications (including RF, microwave, and infrared communications), electronic communications, or other such communication means.

Although the invention has been described with reference to specific exemplary embodiments, it is noted that various modifications and changes may be made to these embodiments without departing from the broad spirit and scope of the invention. For example, the various operations, blocks, etc., described herein may be enabled and operated using hardware circuitry (for example, complementary metal oxide semiconductor (CMOS) based logic circuitry), firmware, software and/or any combination of hardware, firmware, and/or software (for example, embodied in a machine-readable medium). For example, the apparatuses and methods may be embodied using transistors, logic gates, and electrical circuits (for example, application specific integrated circuit (ASIC) circuitry and/or in Digital Signal Processor (DSP) circuitry).

Particularly, the server system 200 and its various components may be enabled using software and/or using transistors, logic gates, and electrical circuits (for example, integrated circuit circuitry such as ASIC circuitry). Various embodiments of the invention may include one or more computer programs stored or otherwise embodied on a computer-readable medium, wherein the computer programs are configured to cause a processor or computer to perform one or more operations. A computer-readable medium storing, embodying, or encoded with a computer program, or similar language, may be embodied as a tangible data storage device storing one or more software programs that are configured to cause a processor or computer to perform one or more operations. Such operations may be, for example, any of the steps or operations described herein. In some embodiments, the computer programs may be stored and provided to a computer using any type of non-transitory computer readable media. Non-transitory computer readable media include any type of tangible storage media. Examples of non-transitory computer readable media include magnetic storage media (such as floppy disks, magnetic tapes, hard disk drives, etc.), optical magnetic storage media (e.g. magneto-optical disks), CD-ROM (compact disc read only memory), CD-R (compact disc recordable), CD-R/W (compact disc rewritable), DVD (Digital Versatile Disc), BD (BLU-RAY® Disc), and semiconductor memories (such as mask ROM, PROM (programmable ROM), EPROM (erasable PROM), flash memory, RAM (random access memory), etc.). Additionally, a tangible data storage device may be embodied as one or more volatile memory devices, one or more non-volatile memory devices, and/or a combination of one or more volatile memory devices and non-volatile memory devices. In some embodiments, the computer programs may be provided to a computer using any type of transitory computer readable media. Examples of transitory computer readable media include electric signals, optical signals, and electromagnetic waves. Transitory computer readable media can provide the program to a computer via a wired communication line (e.g., electric wires, and optical fibers) or a wireless communication line.

Various embodiments of the disclosure, as discussed above, may be practiced with steps and/or operations in a different order, and/or with hardware elements in configurations, which are different than those which are disclosed. Therefore, although the disclosure has been described based upon these exemplary embodiments, it is noted that certain modifications, variations, and alternative constructions may be apparent and well within the spirit and scope of the disclosure.

Although various exemplary embodiments of the disclosure are described herein in a language specific to structural features and/or methodological acts, the subject matter defined in the appended claims is not necessarily limited to the specific features or acts described above. Rather, the specific features and acts described above are disclosed as exemplary forms of implementing the claims.

What is claimed is:

1. A method for controlling a tactile output of an adult toy, the method comprising: receiving, by a system, a user input from a user device associated with a first user of a plurality of users, the user input comprising an interaction information for controlling the tactile output of a second adult toy associated with a second user of the plurality of users, wherein the interaction information comprises an audio input; generating, by the system, a control pattern in response to the interaction information from the first user, the control pattern comprising parameters related to at least one of timing and intensity of the tactile output corresponding to the interaction information, wherein generating the control pattern in response to receipt of the audio input comprises: converting, by the system, the audio input into a text format; and generating, by the system, the control pattern based on the text format of the audio input; and transmitting, by the system, the control pattern to a user device associated with the second user for operating the second adult toy to provide the tactile output to the second user, wherein the tactile output of the control pattern proportionally reproduces the interaction information provided by the first user.

2. The method as claimed in claim 1, wherein the interaction information further comprises at least one of a text input, and a gesture input provided in an interactive application installed on the user device of the first user.

3. The method as claimed in claim 2, wherein generating the control pattern based on receipt of the audio input further comprises:

generating, by the system, the control pattern based at least, in part on, an amplitude associated with the audio input.

4. The method as claimed in claim 1, further comprising:

receiving, by the system, an input from the first user related to sexuality type;

filtering, by the system, one or more users from the plurality of users based on receipt of the input related to the sexuality type; and facilitating, by the system, displaying at the user device of the first user, the control pattern associated with the one or more users of the plurality of users based at least, in part on, the sexuality type.

5. The method as claimed in claim 1, further comprising:

receiving, by the system, an input from the first user related to visibility of the control pattern associated with the first user to other users of the plurality of users of an interactive application; and facilitating, by the system, displaying at the user device of the first user, the control pattern associated with the first user to the other users of the plurality of users based at least, in part on, the input related to the visibility of the control pattern.

6. The method as claimed in claim 1, further comprising:

receiving, by the system, one or more control patterns from the first user of the plurality of users, wherein one or more parameters related to sequence, and playback speed associated with each control pattern of the one or more control patterns are adjusted by providing inputs in an interactive application by the first user; and creating, by the system, a new control pattern by combining the one or more control patterns based at least, in part on, the sequence associated with the each control pattern of the one or more control patterns.

7. The method as claimed in claim 1, further comprising:

transmitting, by the system, a broadcast code received from a broadcast host of an interactive application to the plurality of users;

receiving, by the system, a confirmation message indicative of approval for broadcasting show from at least one user of the plurality of users based at least on entering the broadcast code by the at least one user in the interactive application;

sending, by the system, the confirmation message related to the approval for the broadcasting show from the at least one user to the broadcast host; and facilitating, by the system, broadcasting a control pattern received from the broadcast host to the at least one user of the plurality of users for enabling the adult toy of the at least one user to vibrate along with the adult toy associated with the broadcast host during the broadcasting show.

8. The method as claimed in claim 7, wherein the broadcast code comprises at least one of a quick response (QR) code, and an alphanumeric code.

9. A system for controlling a tactile output of an adult toy, the system comprising:

a communication interface;

a memory storing executable instructions; and a processor operatively coupled with the communication interface and the memory, the processor configured to execute the executable instructions to cause the system to at least:

receive a user input from a user device associated with a first user of a plurality of users, the user input comprising an interaction information for controlling the tactile output of a second adult toy associated with a second user of the plurality of users, wherein the interaction information comprises an audio input, generate a control pattern in response to the interaction information from the first user, the control pattern comprising parameters related to at least one of timing and intensity of the tactile output corresponding to the interaction information, wherein, to generate the control pattern, the system is further caused to:

convert the audio input into a text format; and generate the control pattern based at least on the text format of the audio input, and transmit the control pattern to a user device associated with the second user for operating the second adult toy to provide the tactile output to the second user, the tactile output of the control pattern proportionally reproducing the interaction information provided by the first user.

10. The system as claimed in claim 9, wherein the interaction information further comprises at least one of a text input, and a gesture input provided in an interactive application installed on the user device of the first user.

11. The system as claimed in claim 10, wherein the system is further caused to:

generate the control pattern based at least, in part on, amplitude associated with the audio input.

12. The system as claimed in claim 9, wherein the system is further caused to:

receive an input from the first user related to sexuality type;

filter one or more users from the plurality of users based on receipt of the input related to the sexuality type; and facilitate displaying at the user device of the first user, the control pattern associated with the one or more users of the plurality of users based at least, in part on, the sexuality type.

13. The system as claimed in claim 9, wherein the system is further caused to:

receive an input from the first user, related to visibility of the control pattern associated with the first user to other users of the plurality of users of an interactive application; and facilitate displaying at the user device of the first user, the control pattern associated with the first user to the other users of the plurality of users based at least, in part on, the input related to the visibility of the control pattern.

14. The system as claimed in claim 9, wherein the system is further caused to:

receive one or more control patterns from the first user of the plurality of users, wherein one or more parameters related to sequence, and playback speed associated with each control pattern of the one or more control patterns are adjusted by providing inputs in an interactive application by the first user; and create a new control pattern by combining the one or more control patterns based at least, in part on, the sequence associated with the each control pattern of the one or more control patterns.

15. The system as claimed in claim 9, wherein the system is further caused to:

transmit a broadcast code received from a broadcast host of an interactive application to the plurality of users;

receive a confirmation message indicative of approval for broadcasting show from at least one user of the plurality of users based at least on entering the broadcast code by the at least one user in the interactive application;

send the confirmation message related to the approval for the broadcasting show from the at least one user to the broadcast host; and facilitate broadcasting a control pattern received from the broadcast host to the at least one user of the plurality of users for enabling the adult toy of the at least one user to vibrate along with the adult toy associated with the broadcast host during the broadcasting show.

16. The system as claimed in claim 15, wherein the broadcast code comprises at least one of a quick response (QR) code, and an alphanumeric code.

* * * * *